(12) United States Patent
Bhattacharya et al.

(10) Patent No.: US 12,419,889 B2
(45) Date of Patent: Sep. 23, 2025

(54) METHODS OF TREATING CHRONIC SPONTANEOUS URTICARIA USING A BRUTON'S TYROSINE KINASE INHIBITOR

(71) Applicant: NOVARTIS AG, Basel (CH)

(72) Inventors: Souvik Bhattacharya, Weymouth, MA (US); Bruno Bieth, Saint-Louis (FR); Maciej Cabanski, Allschwil (CH); Bruno Cenni, Sissach (CH); Stefan De Buck, Buesserach (CH); Martin Kaul, Neustadt (DE); Arvind Kinhikar, Cambridge, MA (US); Andrijana Radivojevic, New York, NY (US); Thomas Severin, Freiburg (DE); Julian Storim, Basel (CH); Alessandra Vitaliti Garami, Oberwil (CH)

(73) Assignee: Novartis AG, Basel (CH)

( * ) Notice: Subject to any disclaimer, the term of this patent is extended or adjusted under 35 U.S.C. 154(b) by 975 days.

(21) Appl. No.: 17/612,778

(22) PCT Filed: May 20, 2020

(86) PCT No.: PCT/IB2020/054755
§ 371 (c)(1),
(2) Date: Nov. 19, 2021

(87) PCT Pub. No.: WO2020/234782
PCT Pub. Date: Nov. 26, 2020

(65) Prior Publication Data
US 2022/0184074 A1    Jun. 16, 2022

Related U.S. Application Data

(60) Provisional application No. 62/851,996, filed on May 23, 2019.

(51) Int. Cl.
*A61K 31/505* (2006.01)
*A61P 17/00* (2006.01)
(Continued)

(52) U.S. Cl.
CPC ............ *A61K 31/505* (2013.01); *A61P 17/00* (2018.01)

(58) Field of Classification Search
CPC .............................. A61K 31/505; A61P 17/00
See application file for complete search history.

(56) References Cited

U.S. PATENT DOCUMENTS 9,512,084 B2 * 12/2016 Angst .................. C07D 239/47
10,457,647 B2 * 10/2019 Angst .................. C07D 401/10
11,180,460 B2 * 11/2021 Angst .................. C07D 401/10

FOREIGN PATENT DOCUMENTS

WO     2009038673 A2    3/2009
WO     2015/079417 A1   6/2015
(Continued)

OTHER PUBLICATIONS

Study Protocol for Clinical Trial NCT03926611, Jan. 2019, https://cdn.clinicaltrials.gov/large-docs/11/NCT03926611/Prot_000.pdf (Year: 2019).*

(Continued)

*Primary Examiner* — Jeffrey H Murray
*Assistant Examiner* — Kevin S Martin
(74) *Attorney, Agent, or Firm* — Francine F. Li

(57) ABSTRACT

The present disclosure relates to methods for treating Chronic Spontaneous Urticaria using a compound of Formula (I) or a pharmaceutically acceptable salt thereof. Also disclosed herein is a compound of Formula (I) or a pharmaceutically acceptable salt thereof, for treating Chronic Spontaneous Urticaria patients, as well as medicaments, (Continued)

dosing regimens, pharmaceutical formulations, dosage forms, and kits for use in the disclosed uses and methods.

30 Claims, 11 Drawing Sheets

(51) Int. Cl.
   *A61K 31/513* (2006.01)
   *A61P 37/08* (2006.01)

(56) References Cited

FOREIGN PATENT DOCUMENTS

| WO | 2015105926 A1 | 7/2015 |
| WO | 2016/079669 A1 | 5/2016 |
| WO | 2020234782 A1 | 11/2020 |

OTHER PUBLICATIONS

Walpole SC, Prieto-Merino D, Edwards P, Cleland J, Stevens G, Roberts I. The weight of nations: an estimation of adult human biomass. BMC Public Health. Jun. 18, 2012;12:439. doi: 10.1186/1471-2458-12-439. PMID: 22709383; PMCID: PMC3408371. (Year: 2012).*

Stull D, McBride D, Tian H, Gimenez Arnau A, Maurer M, Marsland A, Balp MM, Khalil S, Grattan C. Analysis of disease activity categories in chronic spontaneous/idiopathic urticaria. Br J Dermatol. Oct. 2017;177(4):1093-1101. doi: 10.1111/bjd.15454. Epub Sep. 24, 2017. PMID: 28295198. (Year: 2017).*

Angst D., "Discovery of LOU064 (Remibrutinib), a Potent and Highly Selective Covalent Inhibitor of Bruton's Tyrosine Kinase", Journal of Medicinal Chemistry, vol. 63(10), pp. 5102-5118, (2020).

Bracken S J., "Autoimmune Theories of Chronic Spontaneous Urticaria", Frontiers in Immunology, vol. 10, pp. 3-7, (2019).

Crawford J J., "Discovery of GDC-0853: a Potent, Selective, and Noncovalent Bruton's Tyrosine Kinase Inhibitor in Early Clinical Development", Journal of Medicinal Chemistry, vol. 61(6), pp. 2227-2245, (2018).

Clinical Trail NCT03926611 publication date Apr. 23, 2019 available at http://clinicaltrials.gov.

Gabizon R., "A Fast and Clean BTK Inhibitor", Journal of Medicinal Chemistry, vol. 63(10), pp. 5100-5101, (2020).

Ferrer, et al., Predicting Chronic Spontaneous Urticaria Symptom Return After Omalizumab Treatment Discontinuation: Exploratory Analysis, J Allergy Clin Immunol Pract, Jul./Aug. 2018, 1191-1197, 6(4).

Godse, et al., Position statement for the use of omalizumab in the management of chronic spontaneous urticaria in Indian patients, Indian Dermatology Online Journal, Jan.-Feb. 2016, 6-11, 7(1).

Pulz, Discovery of LOU064, a covalent BTK inhibitor with best in class selectivity, EFMC-ISMC Symposium Ljubljana, 1-19, Sep. 3, 2018.

Liu, Dermatovenereology diagnosis and treatment-Urticarial Diseases, Hubei Science and Technology Press, 1st edition, chapter 8th, p. 93, 2016.

* cited by examiner

Cpd(I) is compound of Formula (I)

Solid line represents Emax model with 95% confidence intervals (shaded area).

Total daily dose of compound (I) (mg)

METHODS OF TREATING CHRONIC SPONTANEOUS URTICARIA USING A BRUTON'S TYROSINE KINASE INHIBITOR

CROSS-REFERENCE TO RELATED APPLICATIONS

This application is a 371 U.S. National Phase application of International application number PCT/IB2020/054755 filed 20 May 2020, which claims the benefit of U.S. provisional application Ser. No. 62/851,996 filed 23 May 2019; each of which is incorporated by reference herein in its entirety.

TECHNICAL FIELD

The present disclosure relates to methods for treating basophil- and mast-driven skin diseases such as chronic spontaneous urticaria (CSU) using a Bruton's tyrosine kinase inhibitor.

BACKGROUND OF THE DISCLOSURE

Urticaria is a heterogeneous group of diseases characterized by itchy hives and/or angioedema. Chronic urticaria is defined as urticaria that has been continuously or intermittently present for more than 6 weeks (Maurer M et al. (2013) *Revisions to the international guidelines on the diagnosis and therapy of chronic urticaria. J Dtsch Dermatol Ges.*; Bernstein J A, Lang D M, Khan D A, et al (2014) *The diagnosis and management of acute and chronic urticaria: 2014 update. J Allergy Clin Immunol;* 133(5):1270-7). Chronic urticaria is then further divided into two subgroups: Chronic Spontaneous Urticaria (CSU) and Inducible Urticaria (IU) the latter including physical urticaria such as heat-, cold-, or pressure-urticaria, and special variants such as cholinergic urticaria. CSU is defined as spontaneous appearance of itchy wheals, angioedema, or both for a duration of more than 6 weeks due to known or unknown causes (Zuberbier T, et al. (2018) *The EAACI/GA(2) LEN/EDF/WAO Guideline for the definition, classification, diagnosis, and management of urticaria: the 2017 revision and update. Allergy;* 73(7):1393-1414). A combination of both the CSU and an inducible form of urticaria is possible, such as the frequently observed combination of a symptomatic dermographic urticaria and CSU.

Previously, all chronic urticaria forms without a known trigger were named "chronic idiopathic urticaria" (CIU). Due to medical progress, it is now known that in some of the previously considered "idiopathic" urticaria forms in fact auto-antibodies may be detected. However, the daily fluctuating appearance of the symptoms in this chronic urticaria with auto-antibodies still remains unpredictable and is not induced by a demonstrable trigger, hence, symptoms appear spontaneously. In order to reflect in the terminology correctly that some of the former "idiopathic" forms in fact may have detectable auto-antibodies, this population is now referred to as chronic spontaneous urticaria (CSU) according to the international guideline (Maurer M et al. (2013) *Revisions to the international guidelines on the diagnosis and therapy of chronic urticaria. J Dtsch Dermatol Ges.*; Zuberbier T, et al. (2018) *The EAACI/GA(2) LEN/EDF/WAO Guideline for the definition, classification, diagnosis, and management of urticaria: the 2017 revision and update. Allergy;* 73(7):1393-1414). The use of the expression "chronic idiopathic urticaria" in medical practice is no longer recommended. However, this new naming convention is not implemented in all parts of the world, and in countries such as the United States the patient population with chronic urticaria with a non-specific etiology, or unknown triggers is still referred to as chronic idiopathic urticaria (CIU). Following the International Guideline, the disease entity is referred to as CSU throughout this document for consistency.

The lifetime prevalence of CSU is approximately 1.8%, and up 20% of CSU patients may still have the disease after 20 years (Greaves M (2000) *Chronic urticaria. J Allergy Clin Immunol;* 105(4):664-72; Zuberbier T, Balke M, Worm M, et al (2010) *Epidemiology of urticaria: a representative cross-sectional population survey. Clin Exp Dermatol;* 35(8):869-73). Affected patients experience frequent pruritic hives with associated erythema and/or episodes of angioedema. Angioedema is reported to be associated with approximately 33-67% of CSU cases (Juhlin L (1981) *Recurrent urticaria: clinical investigation of 330 patients. Br J Dermatol;* 104(4):369-81; Toubi E, Kessel A, Avshovich N, et al (2004) *Clinical and laboratory parameters in predicting chronic urticaria duration: a prospective study of 139 patients. Allergy;* 59(8):869-73; Zuberbier T, Balke M, Worm M, et al (2010) *Epidemiology of urticaria: a representative cross-sectional population survey. Clin Exp Dermatol;* 35(8):869-73; Maurer M, Weller K, Bindslev-Jensen C, et al (2011) *Unmet clinical needs in chronic spontaneous urticaria. A $GA^2LEN$ task force report. Allergy;* 66(3):317-30). The classic skin lesion in urticaria is a wheal and flare with a pale elevated lesion and surrounding erythema, ranging in size from a few millimeters to a few centimeters across, usually occurring in groups and often coalescing to form large confluent lesions. CSU is associated with intense itching and has a major impact on patient well-being and quality of life, suggested to be comparable to that of severe coronary artery disease (Greaves M W (2003) *Chronic idiopathic urticaria. Curr Opin Allergy Clin Immunol;* 3(5):363-8. Review; Powell R J, Du Toit G L, Siddique N, et al (2007) *BSACI guidelines for the management of chronic urticaria and angio-oedema. Clin Exp Allergy;* 37(5):631-50). The symptoms of urticaria and urticaria-associated angioedema adversely affect daily activities and sleep (O'Donnell B F, Lawlor F, Simpson J, et al (1997). The impact of chronic urticaria on the quality of life. *Br J Dermatol;* 136(2):197-201). Therefore, when managing patients with urticaria, patient-related outcomes (e.g., DLQI) are important measures of treatment (Kaplan A., et al. (2013) *Omalizumab in patients with symptomatic chronic idiopathic/spontaneous urticaria despite standard combination therapy. J Allergy Clin Immunol;* 132(1):101-9; Maurer M et al. (2013) *Revisions to the international guidelines on the diagnosis and therapy of chronic urticaria. J Dtsch Dermatol Ges;* Zuberbier T, Aberer W, Asero R, et al (2018) *The EAACI/GA(2) LEN/EDF/WAO Guideline for the definition, classification, diagnosis, and management of urticaria: the 2017 revision and update. Allergy;* 73(7):1393-1414).

The pathogenesis of CSU is not fully clear. Up to 50% of CSU cases are associated with histamine-releasing autoantibodies against multiple antigens including the high-affinity IgE receptor (FccRI) or IgE antibodies; the clinical significance of these autoantibodies is unclear, though there are suggestions that they may be involved in disease pathogenesis (Kaplan A P (2002) *Chronic urticaria—new concepts regarding pathogenesis and treatment. Curr Allergy Asthma Rep;* 2(4):263-4; Sabroe R A, Greaves M W (2006) *Chronic idiopathic urticaria with functional autoantibodies:* 12 *years on. Br J Dermatol;* 154(5):813-9. Review). It has also been suggested that CSU patients' basophils may have distinct alterations in FcεRIα-mediated degranulation, independent of any potential role of autoantibodies (Eckman J A, et al. (2008) *Basophil phenotypes in chronic idiopathic urticaria in relation to disease activity and autoantibodies. J Invest Dermatol;* 128(8):1956-63).

Treatment of CSU is a challenge and non-sedating (second generation) H1-antihistamines (H1-AH) are the mainstay of symptomatic therapy of CSU. While H1-AH at approved doses provide relief for some patients, more than 50% of patients do not respond to H1l-AH at regular doses. Even when up-dosing to fourfold of the approved dose according to the second step of the treatment algorithm of the current International Guideline (Zuberbier T, et al. (2018) *The EAACI/GA(2) LEN/EDF/WAO Guideline for the definition, classification, diagnosis, and management of urticaria: the 2017 revision and update. Allergy;* 73(7): 1393-1414), a substantial part of patients do not experience control of urticaria symptoms (Maurer M, Weller K, Bindslev-Jensen C, et al (2011) *Unmet clinical needs in chronic spontaneous urticaria. A $GA^2LEN$ task force report. Allergy;* 66(3):317-30; Marrouche N, Grattan C (2014) *Update and insights into treatment options for chronic spontaneous urticaria. Expert Rev Clin Immunol;* 10(3):397-403). For patients without disease control at fourfold doses of H1-AH, the third step of the treatment algorithm of the International Guideline foresees the addition of omalizumab, and after inadequate response to omalizumab, cyclosporin can be used as last-line therapy.

The level of evidence for the efficacy of leukotriene receptor antagonists (LTRA) in urticaria is low. With the availability of omalizumab, (off-label) LTRA are no longer recommended for the treatment of CSU that has not be responsive to H1-antihistamine treatment (Zuberbier 2018). Short courses (max. 10 days) of systemic corticosteroids can be added to the third level treatment regimens, if exacerbations demand this. Due to the adverse effects associated with chronic systemic corticosteroid exposure, a longer duration of treatment is not advisable. Other treatment options that were previously used such as intravenous immunoglobulin G, dapsone, hydroxychloroquine, H2-antihistamines (H2-AH), methotrexate, and cyclophosphamide, have an unfavorable benefit risk profile or significant side-effect profile and are no longer recommended for therapy of CSU (Kaplan A P (2002) *Chronic urticaria—new concepts regarding pathogenesis and treatment. Curr Allergy Asthma Rep;* 2(4):263-4; Powell R J, Du Toit G L, Siddique N, et al (2007) *BSACI guidelines for the management of chronic urticaria and angio-oedema. Clin Exp Allergy;* 37(5):631-50; Zuberbier T, et al. (2018) *The EAACI/GA(2) LEN/EDF/ WAO Guideline for the definition, classification, diagnosis, and management of urticaria: the 2017 revision and update. Allergy;* 73(7):1393-1414).

Omalizumab is an approved therapy for treatment of CSU refractory to standard of care treatment, and exhibits a favorable benefit-risk profile. It is a recombinant humanized $IgG_1$ monoclonal antibody that binds to IgE-specific epitopes within the C3 (FcεRI binding) region of the IgE molecule and is indicated in many countries for the treatment of poorly controlled moderate or severe asthma and CSU refractory to standard therapy. The exact mechanism for how omalizumab may work for CSU patients is unknown. Omalizumab is administered to patients suffering from CSU as an injectable solution.

Despite available treatment for CSU, there remains a high medical need for new treatment options for CSU subjects. Less than 40% of CSU subjects treated with second generation H1-antihistamine do not respond adequately (Guillén-Aguinaga et al 2016, *Br J Dermatol;* 175(6):1153-65). Furthermore, less than 50% of subjects treated with Omalizumab reach a complete control of signs and symptoms of CSU (Kaplan et al. 2016, *J Allergy Clin Immunol;* 137(2):474-81).

SUMMARY OF THE INVENTION

The aim of the invention is to provide novel method of treating or preventing basophil- and mast-driven skin diseases such as chronic spontaneous urticaria and atopic dermatitis in a subject in need of such treatment, comprising administering to said subject, an therapeutically effective amount of N-(3-(6-Amino-5-(2-(N-methylacrylamido) ethoxy)pyrimidin-4-yl)-5-fluoro-2-methylphenyl)-4-cyclopropyl-2-fluorobenzamide.

Therefore, disclosed herein are methods of treating chronic spontaneous urticaria (CSU), comprising administering to a patient in need of such treatment, a daily dose of about 0.5 mg to about 600 mg, preferably a daily dose of about 10 mg to about 200 mg, or more preferably in a daily dose of about 10 mg to about 100 mg of N-(3-(6-Amino-5-(2-(N-methylacrylamido)ethoxy)pyrimidin-4-yl)-5-fluoro-2-methylphenyl)-4-cyclopropyl-2-fluorobenzamide, which is the compound of Formula (I):

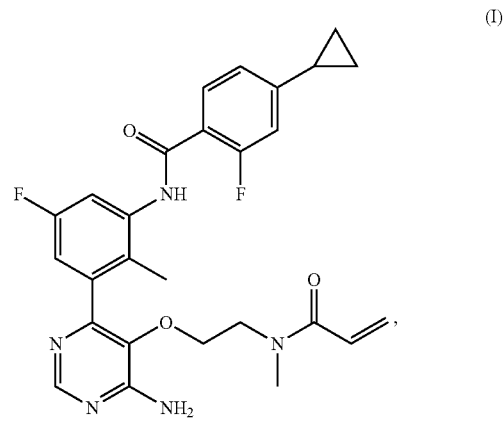 [SMILES: C=CC(=O)N(C)CCOc1c(N)ncnc1-c1cc(F)cc(NC(=O)c2ccc(C3CC3)cc2F)c1C]

or a pharmaceutically acceptable salt thereof.

Also disclosed is N-(3-(6-Amino-5-(2-(N-methylacrylamido)ethoxy)pyrimidin-4-yl)-5-fluoro-2-methylphenyl)-4-cyclopropyl-2-fluorobenzamide; or a pharmaceutically acceptable salt thereof, for use in treating chronic spontaneous urticaria (CSU), wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, is administered in a daily dose of about 0.5 mg to about 600 mg, preferably a daily dose of about 10 mg to about 200 mg, and most preferably in a daily dose of about 10 mg to about 100 mg.

DETAILED DESCRIPTION OF THE DISCLOSURE

Figure 1:
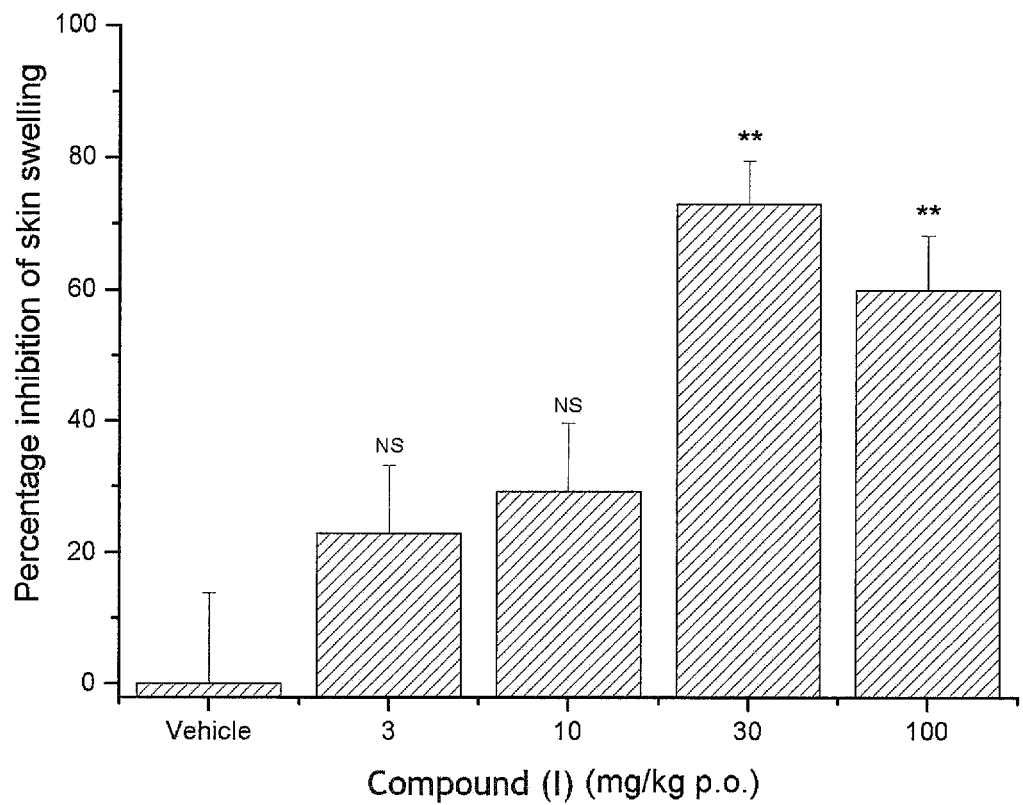
FIG. 1: Inhibitory effects of compound of Formula (I) in the reverse passive arthus reaction

Bruton's tyrosine kinase (BTK) is a cytoplasmic tyrosine kinase and member of the TEC kinase family. BTK is expressed in selected cells of the adaptive and innate immune system including B cells, macrophages, mast cells/basophils and thrombocytes. BTK is indispensable for signaling through the Fc epsilon receptor (FcεR1 for IgE) and the activating Fc gamma receptors (FcγR for IgG), as well as the B cell antigen receptor (BCR) and BTK inhibitors. BTK inhibitors like ibrutinib are approved for the treatment of B cell malignancies (Hendriks et al 2014). Recently, it has been demonstrated that inhibition of BTK leads to inhibition of mast cell and basophil activation/degranulation in vitro and to reduced wheal sizes in skin prick tests with patients suffering from IgE-mediated allergies (Smiljkovic et al 2017; Regan et al 2017; Dispenza et al 2018). Therefore, inhibition of BTK is an attractive therapeutic concept to treat various autoimmune and chronic inflammatory diseases, including rheumatoid arthritis, multiple sclerosis, systemic lupus erythematosus, chronic urticaria, atopic dermatitis, asthma, and primary Sjogren's Syndrome (Tan et al 2013; Whang and Chang 2014).

N-(3-(6-Amino-5-(2-(N-methylacrylamido)ethoxy)pyrimidin-4-yl)-5-fluoro-2-methylphenyl)-4-cyclopropyl-2-fluorobenzamide was described in the WO2015/079417 application filed Jun. 4, 2015. This compound is a selective, potent, irreversible covalent inhibitor of Bruton's tyrosine kinase (BTK).

According to this invention, we have demonstrated that N-(3-(6-Amino-5-(2-(N-methylacrylamido)ethoxy)pyrimidin-4-yl)-5-fluoro-2-methylphenyl)-4-cyclopropyl-2-fluorobenzamide effectively inhibits basophil activation in healthy volunteers and in atopic subjects underlying a similar pathomechanism compared to CSU, as measured by the inhibition of CD63 up-regulation. Additionally, we have demonstrated that N-(3-(6-Amino-5-(2-(N-methylacrylamido)ethoxy)pyrimidin-4-yl)-5-fluoro-2-methylphenyl)-4-cyclopropyl-2-fluorobenzamide reduces wheal sizes in skin prick test.

Accordingly, we have now devised dosing regimens for treating CSU patients with the compound N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof.
Definitions:

For purposes of interpreting this specification, the following definitions will apply and whenever appropriate, terms used in the singular will also include the plural and vice versa.

The phrase "pharmaceutically acceptable" as employed herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen, carbon, nitrogen, oxygen, fluorine, iodine and chlorine, such as $^3$H, $^{11}$C, $^{13}$C, $^{14}$C, $^{15}$N, $^{18}$F, and $^{36}$Cl. Accordingly, it should be understood that the present disclosure includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds can generally be prepared by conventional techniques known to those skilled in the art, e.g., using an appropriate isotopically-labeled reagents in place of the non-labeled reagent previously employed.

The term "pharmaceutical combination" as used herein means a product that results from the use or mixing or combining of more than one active ingredient. It should be understood that pharmaceutical combination as used herein includes both fixed and non-fixed combinations of the active ingredients. The term "fixed combination" means that the active ingredients, e.g., a compound of formula (I) or a pharmaceutically acceptable salt thereof, and one or more combination partners, are administered to a patient simultaneously as a single entity or dosage form. The term in such case refers to a fixed dose combination in one unit dosage form (e.g., capsule, tablet, or sachet). The terms "non-fixed combination" or a "kit of parts" both mean that the active ingredients, e.g., a compound of the present disclosure and one or more combination partners and/or one or more co-agents, are administered or co-administered to a patient independently as separate entities either simultaneously, concurrently or sequentially with no specific time limits wherein such administration provides therapeutically effective levels of the two compounds in the body of the patient, especially where these time intervals allow that the combination partners show a cooperative, e.g., an additive or synergistic effect. The term "non-fixed combination" also applies to cocktail therapy, e.g., the administration of three or more active ingredients. The term "non-fixed combination" thus defines especially administration, use, composition or formulation in the sense that the compounds described herein can be dosed independently of each other, i.e., simultaneously or at different time points. It should be understood that the term "non-fixed combination" also encompasses the use of a single agent together with one or more fixed combination products with each independent formulation having distinct amounts of the active ingredients contained therein. It should be further understood that the combination products described herein as well as the term "non-fixed combinations" encompasses active ingredients (including the compounds described herein) where the combination partners are administered as entirely separate pharmaceutical dosage forms or as pharmaceutical formulations that are also sold independently of each other. Instructions for the use of the non-fixed combination are or may be provided in the packaging, e.g., leaflet or the like, or in other information that is provided to physicians and/or medical staff. The independent formulations or the parts of the formulation, products, or compositions, can then be administered simultaneously or chronologically staggered, that is the individual parts of the kit of parts can each be administered at different time points and/or with equal or different time intervals for any part of the kit of parts. Particularly, the time intervals for the dosing are chosen such that the effect on the treated disease with the combined use of the parts is larger/greater than the effect obtained by use of only compound of Formula (I) or a pharmaceutically acceptable salt thereof; thus the compounds used in pharmaceutical combination described herein are jointly active. The ratio of the total amounts of a compound of formula (I) or a pharmaceutically acceptable salt thereof, to a second agent to be administered as a pharmaceutical combination can be varied or adjusted in order to better accommodate the needs of a particular patient sub-population to be treated or the needs of the single patient, which can be due, for example, to age, sex, body weight, etc. of the patients.

The terms "co-administration" or "combined administration" or the like as utilized herein are meant to encompass the administration of one or more compounds described herein together with a selected combination partner to a single subject in need thereof (e.g., a patient or subject), and are intended to include treatment regimens in which the compounds are not necessarily administered by the same route of administration and/or at the same time.

The term "pharmaceutical composition" is defined herein to refer to a mixture (e.g., a solution or an emulsion) containing at least one active ingredient or therapeutic agent to be administered to a warm-blooded animal, e.g., a mammal or human, in order to prevent or treat a particular disease or condition affecting the warm-blooded animal.

The term "a therapeutically effective amount" of a compound (i.e. compound of Formula (I) or a pharmaceutically acceptable salt thereof) of the present disclosure refers to an amount of the compound of the present disclosure that will elicit the biological or medical response of a subject (patient of subject), for example, reduction or inhibition of an enzyme or a protein activity, or ameliorate symptoms, alleviate conditions, slow or delay disease progression, or prevent a disease, etc. The therapeutically effective dosage of a compound, the pharmaceutical composition, or the combinations thereof, is dependent on the species of the patient, the body weight, age, sex, and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In a preferred embodiment, the subject is a human. The term "subject" is used interchangeably with "patient" when it refers to human.

As used herein, a subject is "in need of" a treatment if such subject would benefit biologically, medically or in quality of life from such treatment.

As used herein, the phrase "population of patients" is used to mean a group of patients.

The term "comprising" encompasses "including" as well as "consisting," e.g., a composition "comprising" X may consist exclusively of X or may include something additional, e.g., X+Y.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The term "treatment" or "treat" is herein defined as the application or administration of a compound according to the disclosure, (compound of Formula (I), or a pharmaceutically acceptable salt thereof, or a pharmaceutical composition comprising said compound, to a subject or to an isolated tissue or cell line from a subject, where the subject has a particular disease (e.g., CSU), a symptom associated with the disease (e.g., CSU), or a predisposition towards development of the disease (e.g., CSU) (if applicable), where the purpose is to cure (if applicable), delay the onset of, reduce the severity of, alleviate, ameliorate one or more symptoms of the disease, improve the disease, reduce or improve any associated symptoms of the disease or the predisposition toward the development of the disease. The term "treatment" or "treat" includes treating a patient suspected to have the disease as well as patients who are ill or who have been diagnosed as suffering from the disease or medical condition, and includes suppression of clinical relapse.

As used herein, the phrases "has not been previously treated with a systemic treatment for CSU" or "naïve" refer to a CSU patient who has not been previously treated with a systemic agent, e.g., cyclosporin A, montelukast, H1-antihistamines (H1-AH), H2-antihistamine (H2-AH), a leukotriene receptor antagonist (LTRA), a biological (e.g., omalizumab.), etc., for CSU. Systemic agents (i.e., agents given orally, by injection, etc.) differ from local agents (e.g., topicals and phototherapy) in that systemic agents have a systemic (whole body) effect when delivered to a patient. In some embodiments of the disclosed methods, regimens, uses, kits, and pharmaceutical compositions, the patient has not been previously administered a systemic treatment for CSU.

As used herein, the phrase "has been previously treated with a systemic agent for CSU" is used to mean a patient that has previously undergone CSU treatment using a systemic agent. Such patients include those previously treated with H1-antihistamine, or biologics, such as omalizumab, and those previously treated with non-biologics, such as cyclosporine. In some embodiments of the disclosure, the patient has been previously administered a systemic agent for CSU. In some embodiments, the patient has been previously administered a systemic agent for CSU (e.g., cyclosporine), but the patient has not been previously administered a systemic biological drug (i.e., a drug produced by a living organism, e.g., antibodies, receptor decoys, etc.) for CSU (e.g., omalizumab). In this case, the patient is referred to as "biological-naïve." In some embodiments, the patient is biological-naïve.

As used herein, "selecting" and "selected" in reference to a patient is used to mean that a particular patient is specifically chosen from a larger group of patients on the basis of (due to) the particular patient having a predetermined criteria. Similarly, "selectively treating" refers to providing treatment to a patient having a particular disease, where that patient is specifically chosen from a larger group of patients on the basis of the particular patient having a predetermined criterion. Similarly, "selectively administering" refers to administering a drug to a patient that is specifically chosen from a larger group of patients on the basis of (due to) the particular patient having a predetermined criterion. By "selecting", "selectively treating" and "selectively administering", it is meant that a patient is delivered a personalized therapy based on the patient's personal history (e.g., prior therapeutic interventions, e.g., prior treatment with biologics), biology (e.g., particular genetic markers), and/or manifestation (e.g., not fulfilling particular diagnostic criteria), rather than being delivered a standard treatment regimen based solely on the patient's membership in a larger group. Selecting, in reference to a method of treatment as used herein, does not refer to fortuitous treatment of a patient having a particular criterion, but rather refers to the deliberate choice to administer treatment to a patient based on the patient having a particular criterion. Thus, selective treatment/administration differs from standard treatment/administration, which delivers a particular drug to all patients having a particular disease, regardless of their personal history, manifestations of disease, and/or biology. In some embodiments, the patient was selected for treatment based on having CSU.

Embodiments of the Invention:
Chronic Urticaria and Effectiveness of Treatment According to the Invention The disclosed BTK inhibitor, i.e., compound of Formula (I), or a pharmaceutically acceptable salt thereof, may be used in vitro, ex vivo, or incorporated into pharmaceutical compositions and administered in vivo to treat CSU patients (e.g., human patients).

Urticaria is a heterogeneous group of diseases characterized by itchy hives and/or angioedema.

Chronic urticaria is defined as urticaria that has been continuously or intermittently present for more than 6 weeks (Maurer, et al 2013, Bernstein, et al 2014). Chronic urticaria is then further divided into two subgroups: Chronic Spontaneous Urticaria (CSU) and Inducible Urticaria (IU) the latter including physical urticaria such as heat-, cold-, or pressure-urticaria, and special variants such as cholinergic urticaria. CSU is defined as spontaneous appearance of itchy wheals, angioedema, or both ≥6 weeks due to known or unknown causes (Zuberbier, et al 2018). A combination of both the CSU and an inducible form of urticaria is possible, such as the frequently observed combination of asymptomatic dermographic urticaria and CSU.

The effectiveness of a CSU treatment is assessed using various known methods and tools that measure CSU disease state and/or CSU clinical response. Some examples include, e.g., Urticaria Patient Daily Diary (UPDD), Angioedema Activity Score (AAS), Weekly Hives Severity Score (HSS7), Weekly Itch Severity Score (IS S7), Weekly Urticaria Activity Score (UAS7) and improvement of health-related quality of life as measure by the Dermatology Life Quality Index (DLQI).

Urticaria Patient Daily Diary (UPDD)

UPDD includes Urticaria Activity Score (UAS) which assesses twice daily severity of itch and number of hives, use of rescue medication, sleep and activity interference, angioedema occurrence, its management and records the calls to an healthcare professional (HCP).

The components are presented in the Table 1 and the relevant weekly scores are described below:

TABLE 1

UPDD

| Diary component | When assessed |
|---|---|
| Urticaria Activity Score (UAS) | Morning & evening |
| Itch severity | |
| Number of hives | |
| Sleep interference Morning | Morning |
| Daily activity interference Evening | Evening |
| Rescue medication use Evening | Evening |
| Angioedema | |
| Whether patient had an episode | |
| If patient had an episode, how did they manage it | |
| Contact health care provider | Evening |

In some embodiments, when a population of CSU patients is treated according to the disclosed methods, patient achieves an improved UPDD score.

Weekly Hives Severity Score (HSS7)

The hives (wheals) severity score, defined by number of hives, is recorded by the subject twice daily in their eDiary, on a scale of 0 (none) to 3 (>12 hives/12 hours; Table 2). A weekly score (HSS7) is derived by adding up the average daily scores of the 7 days preceding the visit. The possible range of the weekly score is therefore 0-21.

TABLE 2

Hives Severity Score

| Score | Hives (Wheals) (every 12 hours) |
|---|---|
| 0 | None |
| 1 | 1-6 hives/12 hours |

TABLE 2-continued

Hives Severity Score

| Score | Hives (Wheals) (every 12 hours) |
|---|---|
| 2 | 7-12/12 hours |
| 3 | >12 hives/12 hours |

In some embodiments, when a population of CSU patients is treated according to the disclosed methods, the hive severity score (HSS7) improves by at least 5 points. Furthermore, when compared to the placebo group, a difference between the treated group and the placebo group is at least 4 points, preferably at least 5 points. In one embodiment, when a patient is treated according to the disclosed methods, the hive severity score (HSS7) is less than 6, preferably less than 4, preferably less than 2, and most preferably the HSS7 score is 0.

Weekly Itch Severity Score (ISS7)

The severity of the itch is recorded by the subject twice daily in their eDiary, on a scale of 0 (none) to 3 (severe) (Table 3). A weekly score (ISS7) is derived by adding up the average daily scores of the 7 days preceding the visit. The possible range of the weekly score is therefore 0-21.

TABLE 3

Itch Severity Score

| Score | Pruritus (Itch) (every 12 hours) |
|---|---|
| 0 | None |
| 1 | Mild (minimal awareness, easily tolerated) |
| 2 | Moderate (definite awareness, bothersome but tolerable) |
| 3 | Severe (difficult to tolerate) |

In some embodiments, when a population of CSU patients are treated according to the disclosed methods, the itch severity score (ISS7) improves by at least 5 point. Furthermore, when compared to the placebo group, a difference between the treated group and the placebo group is at least 4 points, preferably at least 5 points. In one embodiment, when a patient is treated according to the disclosed methods, the itch severity score (ISS7) is less than 6, preferably less than 4, preferably less than 2, and most preferably the ISS7 score is 0.

Weekly Urticaria Activity Score (UAS7)

The UAS7 is the sum of the HSS7 score and the ISS7 score. The possible range of the weekly UAS7 score is 0-42 (highest activity).

In some embodiments, a CSU patient achieves an improved UAS7 in response to treatment with compound of Formula (I) or a pharmaceutically acceptable salt thereof.

In a preferred embodiment, when treated in a method of the invention, a CSU patient has a reduction of hives and itch characterized by UAS7≤6 by week 4, or by week 12.

In most preferred embodiment, when treated in a method of the invention, a CSU patient has a complete absence of hives and itch by week 12, assessed as UAS7=0.

Furthermore, when compared to the placebo group, a difference between the treated group and the placebo group is at least 8 points, preferably at least 10 points.

Weekly Sleep Interference Score

Sleep interference is assessed by the subject, once daily in the morning in the eDiary. It is scored on a scale from 0 to 3. The weekly score ranges from 0 to 21 (Table 4).

TABLE 4

Sleep interference score

| Score | Sleep interference |
|---|---|
| 0 | No interference |
| 1 | Mild, little interference with sleep |
| 2 | Moderate, awoke occasionally, some interference with sleep |
| 3 | Substantial, woke up often, severe interference with sleep |

In some embodiments, when a population of CSU patients are treated according to the disclosed methods, the sleep interference score improves by at least 5 points. In a preferred embodiment, when a patient is treated according to the disclosed methods, the sleep interference score is less than 6, preferably less than 4, preferably less than 2, and most preferably the sleep interference score is 0.

Weekly Activity Interference Score

Activity interference is assessed by the subjects on a scale of 0 to 3, once daily in the evening in the eDiary. Daily activities could include work, school, sports, hobbies and activities with friends and family. A weekly activity interference score ranges from 0 to 21 (Table 5).

TABLE 5

Activity interference score

| Score | Activity interference |
|---|---|
| 0 | No interference |
| 1 | Mild, little interference with daily activities |
| 2 | Moderate, some interference with daily activities |
| 3 | Substantial, severe interference with daily activities |

In some embodiments, when a population of CSU patients are treated according to the disclosed methods, the activity interference score improves by at least 5 points. In a preferred embodiment, when a patient is treated according to the disclosed methods, the weekly activity interference score is less than 6, preferably less than 4, preferably less than 2, and most preferably the weekly activity interference score is 0.

H1-Antihistamine Rescue Medication Use

The number of tablets of rescue medication used over the past 24 hours to control conditions such as itch or hives is recorded once daily in the evening in the eDiary by the subject. The dose per day of rescue medication is calculated as the daily number of tablets times the dose of each tablet, then the dose per week of rescue medication is calculated as the sum of the dose per day, over 7 days.

In some embodiments, when a population of CSU patients are treated according to the disclosed methods, the number of dose per week or rescue medication is decreased. In one aspect of this embodiment, the use of rescue medication is no longer necessary.

Number of Calls to Doctor or Nurse

The number of calls to doctor, nurse or nurse practitioner because of the subject's skin condition is recorded once daily in the eDiary by the subject.

Angioedema Activity Score (AAS)

AAS is recorded once daily in the evening in the eDiary by the subject. This validated tool assesses occurrence and severity of episodes of angioedema (Weller et al (2013), Allergy 68(9): 1185-92). Angioedema occurrence is recorded once daily in the evening in the eDiary by the subject. Actions and/or treatments related to those angioedema occurrences is also recorded in the eDiary as follows (multiple answers possible):
- Did nothing
- Took some prescription or non-prescription medication
- Called my doctor, nurse or nurse practitioner
- Went to see my doctor, nurse or nurse practitioner
- Went to the emergency room at the hospital
- Was hospitalized If subjects answer an opening question with "no", AAS score for this day is 0. If "yes" is the answer to the opening question, the subject continue to answer questions about the duration, severity and impact on daily functioning and appearance of the angioedema.

A score between 0 and 3 is assigned to every answer field. The AAS score in this study is reported as weekly AAS (AAS7). Minimum and maximum possible AAS7 scores are 0-105. Higher score means higher severity.

In some embodiments, when a population of CSU patients are treated according to the disclosed methods, patients achieve a reduction in the AAS7 score, preferably an AAS7 score of 0 by week 12 of treatment. In another aspect of this embodiment, the patient achieves an AAS7 score of zero over several weeks, for example over at least 4 weeks of treatment, over at least 8 weeks of treatment or over the entire 12 weeks of treatment.

In some embodiments, when a population of CSU patients are treated according to the disclosed methods, patients achieve ≥95.5% of angioedema free days (AAS=0) from week 4 to week 12.

Furthermore, when compared to the placebo group, a difference between the treated group and the placebo group is at least 6%.

Dermatology Life Quality Index (DLQI)

The Dermatology Life Quality Index (DLQI) is dermatology specific quality of life (QoL) measure (Finlay et al 1994). The DLQI was validated for patients aged 16 and above. Subjects rate their dermatology symptoms as well as the impact of their skin condition on various aspects of their lives thinking about the previous 7 days.

An overall score is calculated and ranges from 0 to 30 (higher score meaning worse disease related QoL). Domain scores are calculated for: Symptoms and Feelings (0-6), Daily Activities (0-6), Leisure (0-6), Work and School (0-3), Personal Relationships (0-6), Treatment (0-3). The overall DLQI score range was split into score bands (Hongbo et al 2005) and validated in terms of their meaning/relevance to patients as follows:

TABLE 6

DLQI score bands and impact on patient's life

| DLQI band | Significance of score |
|---|---|
| 0-1 | No effect on patient's life |
| 2-5 | Small effect on patient's life |
| 6-10 | Moderate effect on patient's life |
| 11-20 | Very large effect on patient's life |
| 21-30 | Extremely large effect on patient's life |

A DLQI score of >10 is relevant for a very large impact on patients' life and justification for a biologic prescription for example in psoriasis (Kaplan et al 2005). The DLQI questionnaires are completed at randomization (Day 1), Weeks 4 (Day 29) and Week 12 (Day 85) in the eDiary. The DLQI should be completed prior to any other assessment and prior to administration of Compound of Formula (I) or a pharmaceutically acceptable salt thereof.

In some embodiments, a CSU patient achieves an improved DLQI in response to treatment with compound of Formula (I) or a pharmaceutically acceptable salt thereof. In some embodiment, the CSU patient achieve a DLQI score of 0 or 1 at week 4, or at week 12 of treatment.

Chronic Urticaria Index (CU Index)

The CU-Index® is a commercially available in vitro basophil histamine release assay in which a patient's serum is mixed with donor basophils and the released histamine levels are measured through a quantitative enzyme immunoassay. A CU-Index value of greater than or equal to 10 indicates that the patient has either an autoimmune basis for their disease (auto-antibodies for IgE, FcεRI, or anti-FcεRII; a positive result does not indicate which autoantibody) or an alternate histamine-releasing factor (Biagtan M J, Viswanathan R K, Evans M D, et al (2011) *Clinical utility of the Chronic Urticaria Index. J Allergy Clin Immunol;* 127(6): 1626-7).

In some embodiments, a CSU patient experiences in response to treatment with compound of Formula (I) or a pharmaceutically acceptable salt thereof, a decrease in titers of CSU-pathogenesis associated antibodies (e.g. auto-antibodies for IgE, FcεRI, or anti-FcεRII).

In another embodiment, a CSU patient experiences, in response to treatment with compound of Formula (I) or a pharmaceutically acceptable salt thereof, a decrease in the CU index value. In some embodiment, a CSU patient achieves a reduction of CU index to less than 10 at week 4, or at week 12 of treatment.

In some embodiments, the patient is treated for CSU according to the claimed methods for at least 4 weeks, at least 12 weeks, at least 16 weeks, at least 48 weeks, or at least 2 years.

In a preferred embodiment, the patient previously had an inadequate response to conventional systemic CSU therapy (e.g. second generation H1-antihistamine).

In another preferred embodiments, the patient is an adult patient (≥18 years of age) having moderate to severe CSU. Moderate to severe CSU is defined as a patient having a 7-day Urticaria Activity score (UAS7)≥16 and/or a 7-day Hives Severity Score (HSS7)≥8.

In some embodiments, in response to treatment according to the claimed methods, the patient experiences rapid reduction of hives itch, as measured by UAS7 scoring, as early as 4 week after initial dosing, or at week 12 after initial dosing. In a preferred embodiment, the patient experiences a reduction of hives and itch achieving a UAS7 score ≤6 at week 4 or at week 12. In a most preferred embodiment, the patient experiences a complete absence of hives and itch (UAS7=0) at week 4 or at week 12.

In some embodiments, in response to treatment according to the claimed methods, the patient experiences rapid reduction in frequency and severity of angiodema, as measured by AAS7 scoring, as early as 4 week after initial dosing, or at 12 weeks after initial dosing. In one embodiment, the patient experiences a complete absence of angiodema throughout at least 8 weeks of the 12 weeks treatments (as measured by an AAS7 score of zero for a period of at least 8 weeks of the 12 weeks treatment). In a preferred embodiment, the patient experiences a complete absence of angiodema throughout the entire treatment (as measured by an AAS7 score of zero for the period of 12 weeks).

In some embodiments, in response to treatment according to the claimed methods, the patient experiences a decrease in titers of CSU-pathogenesis associated antibodies (auto-antibodies for IgE, FcεRI, or anti-FcεRII) and/or a decrease in the CU index value to less than 10.

Pharmaceutical Composition

The BTK inhibitor, i.e., compound of Formula (I), or a pharmaceutically acceptable salt thereof, may be used as a pharmaceutical composition when combined with a pharmaceutically acceptable carrier. Such a composition may contain, in addition to the compound of Formula (I) or a pharmaceutically acceptable salt thereof, carriers, various diluents, fillers, salts, buffers, stabilizers, solubilizers, and other materials known in the art. The characteristics of the carrier depends on the route of administration. The pharmaceutical compositions for use in the disclosed methods may also contain additional therapeutic agents for treatment of the particular targeted disorder. For example, a pharmaceutical composition may also include anti-inflammatory or anti-itch agents. Such additional factors and/or agents may be included in the pharmaceutical composition to produce a synergistic effect with the compound of Formula (I) or a pharmaceutically acceptable salt thereof, or to minimize side effects caused by the compound of Formula (I) or a pharmaceutically acceptable salt thereof. In preferred embodiments, the pharmaceutical composition for use in the disclosed methods comprise compound of Formula (I) or a pharmaceutically acceptable salt thereof, in a dose of about 5 mg, about 10 mg, about 20 mg, about 25 mg, about 50 mg or about 100 mg.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients, which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Pharmaceutical compositions for use in the disclosed methods may be manufactured in conventional manner. In one embodiment, the pharmaceutical composition is provided for oral administration. For example the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Combinations:

In practicing some of the methods of treatment or uses of the present disclosure, a therapeutically effective amount of a compound of Formula (I) or a pharmaceutically acceptable salt thereof, is administered to a patient, e.g., a mammal (e.g., a human). While it is understood that the disclosed methods provide for treatment of CSU patients using compound of Formula (I) or a pharmaceutically acceptable salt thereof, the therapy is not necessarily a monotherapy. Indeed, if a patient is selected for treatment with a compound of Formula (I) or a pharmaceutically acceptable salt thereof, then the compound of Formula (I) may be administered in accordance with the methods of the disclosure either alone or in combination with other agents and therapies for treating CSU patients, e.g., in combination with at least one additional CSU agent. When co-administered with one or more additional CSU agent(s), a compound of Formula (I) or a pharmaceutically acceptable salt thereof, may be administered either simultaneously with the other agent, or sequentially. If administered sequentially, the attending physician will decide on the appropriate sequence of administering the compound of Formula (I), in combination with other agents and the appropriate dosages for co-delivery.

Various therapies may be beneficially combined with the disclosed compound of Formula (I), during treatment of CSU. Such therapies include topical treatments (creams [non-steroidal or steroidal], washes, antiseptics,), systemic treatments (e.g., with biologicals, antibiotics, or chemical entities), and antiseptics, photodynamic therapy, and surgical intervention (laser, draining or incision, excision).

Non-limiting examples of topical CSU agents for use with the disclosed compound of Formula (I) or a pharmaceutically acceptable salt thereof, include benzoyl peroxide, topical steroid creams, topical antibiotics in the aminoglycoside group, such as clindamycin, gentamicin, and erythromycin, resorcinol cream, iodine scrubs, and chlorhexidine.

Non-limiting examples of CSU agents used in systemic treatment for use with the disclosed compound of Formula (I) or a pharmaceutically acceptable salt thereof, include IgE antagonists (omalizumab, ligezumab).

Additional CSU agents for use in combination with the disclosed compound of Formula (I), during treatment of CSU include cyclosporine and corticosteroids (injectable or oral).

A skilled artisan will be able to discern the appropriate dosages of the above CSU agents for co-delivery with the disclosed compound of Formula (I) or a pharmaceutically acceptable salt thereof.

Kits of the Invention:

The invention also provides kits for treating CSU. Such kits comprise a BTK inhibitor, e.g. a compound of Formula (I) or a pharmaceutical composition thereof. In one embodiment, the kit comprises two or more two or more separate pharmaceutical compositions, at least one of which contains a compound of Formula (I) or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of Formula (I) or a pharmaceutically acceptable salt thereof and the other CSU agent (as defined herein) may be manufactured and/or formulated by the same or different manufacturers. Moreover, the compound of Formula (I) or a pharmaceutically acceptable salt thereof and the other CSU agent may be brought together into a combination therapy: (i) prior to release of the combination product to physicians (e.g. in the case of a kit comprising a compound of Formula (I) or a pharmaceutically acceptable salt thereof, and the other CSU agent); (ii) by the physician themselves (or under the guidance of the physician) shortly before administration; (iii) in the patient themselves, e.g. during sequential administration of the compound of Formula (I) or a pharmaceutically acceptable salt thereof, and the other CSU agent.

Additional Embodiments

A compound of Formula (I) or a pharmaceutically acceptable salt thereof, is conveniently administered to a patient (preferably orally) in a dose of about 10 mg to about 200 mg daily.

A compound of Formula (I) or a pharmaceutically acceptable salt thereof, is conveniently administered to a patient (preferably orally) in a daily dose of about 10 mg to about 200 mg daily.

In some embodiments, the compound of Formula (I) or a pharmaceutically acceptable salt thereof, is administered in a daily dose of about 10 mg to about 100 mg.

In some embodiments, the compound of Formula (I) or a pharmaceutically acceptable salt thereof, is administered in a daily dose of about 10 mg, about 20 mg, about 25 mg, about 35 mg, about 50 mg, about 100 mg or about 200 mg.

In other embodiments, the compound of Formula (I) or a pharmaceutically acceptable salt thereof, is administered in a daily dose of about 100 mg.

In other embodiments, the compound of Formula (I) or a pharmaceutically acceptable salt thereof, is administered in a daily dose of about 50 mg.

In other embodiments, the compound of Formula (I) or a pharmaceutically acceptable salt thereof, is administered in a daily dose of about 35 mg.

In other embodiments, the compound of Formula (I) or a pharmaceutically acceptable salt thereof, is administered in a daily dose of about 25 mg.

In other embodiments, the compound of Formula (I) or a pharmaceutically acceptable salt thereof, is administered in a daily dose of about 20 mg.

In one embodiment, compound of Formula (I) or a pharmaceutically acceptable salt thereof, is administered once daily in a dose of about 10 mg, about 35 mg, about 50 mg or about 100 mg.

In another embodiment, compound of Formula (I) or a pharmaceutically acceptable salt thereof, is administered twice daily in a dose of about 10 mg, about 25 mg, about 50 mg or about 100 mg.

It will be understood that dose escalation may be required for certain patients, e.g., CSU patients that display inadequate response (e.g., as measured by any of the CSU scoring systems disclosed herein, e.g., The method according to any of the above claims, wherein said patient achieves a sustained response as measured by complete response (Hives and itch Severity Score UAS7) and Dermatology Life Quality Index (DLQI), etc.) to treatment with the compound of Formula (I) or a pharmaceutically acceptable salt thereof, by week 4 or week 12 of treatment. It will also be understood that dose reduction may also be required for certain patients, e.g., CSU patients that display adverse events or an adverse response to treatment with compound of Formula (I) or a pharmaceutically acceptable salt thereof. Thus, dosages of the compound of Formula (I) or a pharmaceutically acceptable salt thereof, may be less than about 10 mg, about 20 mg, about 25 mg, about 50 mg, or about 100 mg.

The timing of dosing is generally measured from the day of the first dose of compound of Formula (I), or a pharmaceutically acceptable salt thereof (which is also known as "baseline"). The timing of dosing is generally measured from the day of the first dose of Compound of Formula (I), or a pharmaceutically acceptable salt thereof (which is also known as "baseline").

However, health care providers often use different naming conventions to identify dosing schedules. For clarification, as disclosed herein, the first day of dosing is referred to as day 1. However, it will be understood by a skilled artisan that this naming convention is simply used for consistency and should not be construed as limiting, i.e., daily dosing is the provision of a daily dose of the compound of Formula (I) and the physician may refer to a particular day as "day 0" or "day 1".

Disclosed herein are methods of treating chronic spontaneous urticaria (CSU), comprising administering to a patient in need thereof, a compound of Formula (I), or a pharmaceutically acceptable salt thereof, in a dose is about 10 mg-about 200 mg.

Also disclosed herein are methods of treating chronic spontaneous urticaria (CSU), comprising administering to a patient in need thereof, a compound of Formula (I), or a pharmaceutically acceptable salt thereof, in a daily dose is about 10 mg-about 200 mg.

Also disclosed herein is a compound of Formula (I), or a pharmaceutically acceptable salt thereof, for use in treating CSU, wherein the daily dose of the compound is about 10 mg-about 200 mg.

In one embodiment of the disclosed methods, uses and kits, the compound of Formula (I), or a pharmaceutically acceptable salt thereof, is administered in a daily dose of about 10 mg to about 100 mg.

In another embodiment of the disclosed methods, uses and kits, the compound of Formula (I), or a pharmaceutically acceptable salt thereof, is administered in a daily dose of about 10 mg, about 20 mg, about 25 mg, about 35 mg, about 50 mg, about 100 mg or about 200 mg.

In another embodiment of the disclosed methods, uses and kits, the compound of Formula (I), or a pharmaceutically acceptable salt thereof, is administered in a daily dose of about 100 mg.

In another embodiment of the disclosed methods, uses and kits, the compound of Formula (I), or a pharmaceutically acceptable salt thereof, is administered in a daily dose of about 50 mg.

In another embodiment of the disclosed methods, uses and kits, the compound of Formula (I), or a pharmaceutically acceptable salt thereof, is administered in a daily dose of about 35 mg.

In another embodiment of the disclosed methods, uses and kits, the compound of Formula (I), or a pharmaceutically acceptable salt thereof, is administered in a daily dose of about 25 mg.

In another embodiment of the disclosed methods, uses and kits, the compound of Formula (I), or a pharmaceutically acceptable salt thereof, is administered in a daily dose of about 20 mg.

In another embodiment of the disclosed methods, uses and kits, the compound of Formula (I), or a pharmaceutically acceptable salt thereof, is administered once daily in a dose of about 10 mg, about 35 mg, about 50 mg, or about 100 mg.

In another embodiment of the disclosed methods, uses and kits, the compound of Formula (I), or a pharmaceutically acceptable salt thereof, is administered in a dose of about 10 mg, about 25 mg, about 50 mg, or about 100 mg twice daily.

In another embodiment of the disclosed methods, uses and kits, prior to treatment with the compound of Formula (I) or a pharmaceutically acceptable salt thereof, the patient has been previously treated with a systemic agent for CSU. In one aspect of this embodiment, the systemic agent is selected from the group consisting of H1-antihistamines (H1-AH), H2-antihistamines (H2-AH), and a leukotriene receptor antagonist (LTRA) and combinations thereof.

In another embodiment of the disclosed methods, uses and kits, prior to treatment with the compound of Formula (I), or a pharmaceutically acceptable salt thereof, the patient has not been previously treated with a systemic agent for CSU.

In another embodiment of the disclosed methods, uses and kits, prior to treatment with the compound of Formula (I) or a pharmaceutically acceptable salt thereof, the patient has moderate to severe CSU; i.e. the patient has a UAS7 score ≥16 and/or a HSS7 score ≥8.

In another embodiment of the disclosed methods, uses and kits, prior to the treatment with the compound of Formula (I) or a pharmaceutically acceptable salt thereof, the patient has either an autoimmune basis for their disease (auto-antibodies for IgE, FcεRI, or anti-FcεRII) or an alternate histamine-releasing factor.

In another embodiment of the disclosed methods, uses and kits, prior to the treatment with the compound of Formula (I) or a pharmaceutically acceptable salt thereof, the patient has a CU index greater than or equal to 10. In a particular aspect of this embodiment, the patient achieves by week 4 or week 12 of treatment a reduction of the CU index to less than 10.

In another embodiment of the disclosed methods, uses and kits, the patient is selected according to at least one of the following criteria:
  a) prior to treatment with compound of Formula (I) or a pharmaceutically acceptable salt thereof, the patient has an UAS7 score of ≥16;
  b) prior to treatment with the compound of Formula (I) or a pharmaceutically acceptable salt thereof, the patient has an HSS7 score ≥8.

In another embodiment of the disclosed methods, uses and kits, the patient is an adult.

In another embodiment of the disclosed methods, uses and kits, the patient achieves by week 4 or week 12 of treatment at least one of the following:
  a) a reduction of hives and itch as measured by a UAS≤6 or a complete absence of hives and itch (UAS7=0);
  b) a Dermatology Life Quality Index (DLQI)=0-1;
  c) an absence of Angioedema as measured by the angiodema activity score (AAS7) of zero.

In another embodiment of the disclosed methods, uses and kits, the patient achieves a sustained response as measured by complete hives and itch response ([UAS7]=0) and/or Dermatology Life Quality Index (DLQI)=0-1 and/or a continued absence of angiodema (AAS7=0) at week 4 after completion of the treatment.

Further Enumerated Embodiments

1. A method of treating chronic spontaneous urticaria (CSU), comprising administering to a subject in need thereof a daily dose of about 10 mg to about 200 mg of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof.

2. The method according to embodiment 1, wherein the daily dose of N (3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 10 mg to about 100 mg.

3. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 100 mg.

4. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 50 mg.

5. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 35 mg.

6. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 25 mg.

7. The method according to embodiment 1, wherein the daily dose of N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof is about 20 mg.

8. The method according to embodiment 1, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, is administered once a day in a dose of about 10 mg, about 35 mg, about 50 mg or about 100 mg.

9. The method according to embodiment 1, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, is administered in a dose of about 10 mg, about 25 mg, about 50 mg or about 100 mg twice daily.

10. The method according to any one of the above embodiments, wherein, prior to treatment, the subject has been previously treated with a systemic agent for CSU.

11. The method according to embodiment 10, wherein the systemic agent is selected from the group consisting of H1-antihistamines (H1-AH), H2-antihistamines (H2-AH), and a leukotriene receptor antagonist (LTRA) and combinations thereof.

12. The method according to any one of embodiments 1-9, wherein, prior to treatment, the subject has not been previously treated with a systemic agent for CSU.

13. The method according to any one of the above embodiments, wherein the subject has moderate to severe CSU.

14. The method according to any one of embodiments 1-13, wherein the subject is selected according to at least one of the following criteria:
   a) prior to treatment with compound of Formula (I) or a pharmaceutically acceptable salt thereof, the subject has an UAS7 score of ≥16;
   b) prior to treatment with the compound of Formula (I) or a pharmaceutically acceptable salt thereof, the subject has an HSS7 score ≥8.

15. The method according to any one of the above embodiments, wherein the subject is an adult.

16. The method according to any one of the preceding embodiments, wherein said subject achieves by week 4 or at week 12 of treatment at least one of the following:
   a) a reduction in hives and itch as measured by a UAS≤6, or a complete absence of hives and itch (UAS7=0); or
   b) a Dermatology Life Quality Index (DLQI)=0-1;
   c) an absence of Angiodema as measured by the angiodema activity score (AAS7) of zero.

17. The method according to any one of the above embodiments, wherein said subject achieves a sustained response as measured by complete hives and itch response ([UAS7]=0) and/or a Dermatology Life Quality Index (DLQI)=0-1 and/or a continued absence of angiodema (AAS7=0) at week 4 after completion of the treatment.

18. The method according to any one of the above embodiments, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or pharmaceutically acceptable salt thereof is disposed in a pharmaceutical formulation, wherein said pharmaceutical formulation further comprises pharmaceutically acceptable carriers.

19. The method according to any one of embodiments 1-18, wherein N-(3-(6-Amino-5-(2-(N-methylacrylamido)ethoxy)pyrimidin-4-yl)-5-fluoro-2-methylphenyl)-4-cyclopropyl-2-fluorobenzamide, or a pharmaceutically acceptable salt thereof, has a $T_{max}$ of about 05-3 hours.

ABBREVIATION

AE adverse effect
AUC area under the curve
AUCinf area under the plasma (or serum or blood) concentration-time curve from time zero to infinity (mass×time/volume)
AUClast area under the plasma (or serum or blood) concentration-time curve from time zero to time of last quantifiable concentration (mass×time/volume)
AUCtau area under the plasma (or serum or blood) concentration-time curve from time zero to the end of the dosing interval tau (mass×time/volume)
b.i.d. twice daily
BMI body mass index
CL/F the apparent systemic (or total body) clearance from plasma (or serum or blood) following administration (mass/volume)
Cmax maximum concentration after drug administration
CSU chronic spontaneous urticaria
ECG electrocardiogram
Emax maximum change in effect over placebo
FcγR Fc gamma receptor
FcεR Fc alpha receptor
MRT Mean residence time
PK Pharmacokinetics
PD Pharmacodynamics
PRO Patient reported outcome
QoL Quality of life
q.d. once a day
QTcF QT interval corrected by Fridericia's formula
SAE serious adverse effect
$T_{max}$ time limit to reach maximum concentration after drug administration
T1/2 the terminal elimination half life
Tlast time of last measureable concentration in PK profile
Vz/F the apparent volume of distribution during the terminal elimination phase following administration (volume)

Example 1: Preclinical Studies

Example 1a: BTK Occupancy and Preclinical PK/PD Relationship

The in vivo PD effects of an irreversible BTK inhibitor like compound (I) are determined by the extent and duration of covalent BTK occupancy by the inhibitor. BTK occupancy after treatment with Compound of Formula (I) (also referenced to as Compound (I)) was measured in an ex vivo immunoassay. The fraction of unoccupied BTK protein was assayed after in vitro incubation with a covalent biotinylated BTK probe, since compound (I) and the probe bind to BTK in a mutually exclusive manner. Unoccupied BTK, as well as total BTK relative protein levels were determined in lysates of selected tissues and levels of unoccupied BTK were normalized to total BTK protein levels in the same samples.

In female rats a single oral dose of 3 mg/kg compound (I) resulted in full spleen BTK occupancy, a dose of 1 mg/kg resulted in 76%-81% occupancy, whereas after a single dose of 0.3 mg/kg only partial occupancy of 30% was reached. BTK occupancy in blood reached levels consistent with those observed in spleen. From the experimental data it was apparent that a short transient systemic exposure of compound (I) is sufficient to achieve full BTK occupancy in several tissues at low oral doses of 1-3 mg/kg. The blood exposure of compound (I) after a 1 mg/kg dose reached 49.1 nM at 0.5 hours and was 5.6 nM at 5 hours post dose. This very low and transient systemic exposure is consistent with the PK/PD model typical of irreversible inhibitors.

The duration of BTK occupancy was determined in rats and mice after single oral dose of compound (I) for spleen, blood, lymph nodes and lung. In rats, BTK occupancy showed a long half-life in blood of approximately 87 hours. The estimated BTK occupancy half-life in rat spleen is significantly shorter than in blood with only approximately 5 hours. The different turnover rates may reflect the fact that BTK expressing B cells and monocytes in peripheral blood are resting and metabolically relatively inactive compared to the spleen. The longer persistence of BTK occupancy in blood has been reported before (Advani et al 2013, *J Clin Onc*; 31(1):88-94). All other tissues analyzed (lung and lymph node) showed a similar BTK turnover and occupancy half-life as spleen.

Example 1B: In Vivo Efficacy in Acute Mouse Models of Cutaneous Hypersensitivity The effects of compound (I) on FcγR- and FcεR-induced hypersensitivity were assessed in two acute cutaneous mouse models. Because of the less favorable PK of compound (I) in the mouse, the compound was dosed twice daily.

The duration of the PD effect in skin after single dose was assessed in the reverse passive Arthus (RPA) model of mast cell FcγRIII—mediated inflammation. In this RPA model, a polyclonal IgG antibody is injected locally into the dermis, while the soluble antigen is given systemically by i.v. injection. In this mouse model, mast cell FcγRIII has a dominant role with only minor contributions by the complement system (Hazenbos et al. 1998, journal of immunology, 161(6), pp. 3026; Hazenbos et al., Immunity, 1996, 5(2), pp. 181; Köhl & Gessner 1999, Molecular immunology, 36(13-14), pp. 893; Sylvestre & Ravetch 1996, Immunity, 5(4), pp. 387; Sylvestre & Ravetch 1994, Science, 265(5175), pp. 1095). It has been shown that genetic BTK deficient mice are protected in the passive Arthus skin reaction (Fiedler et al. 2011, blood, 117(4), pp. 1329).

Figure 2:
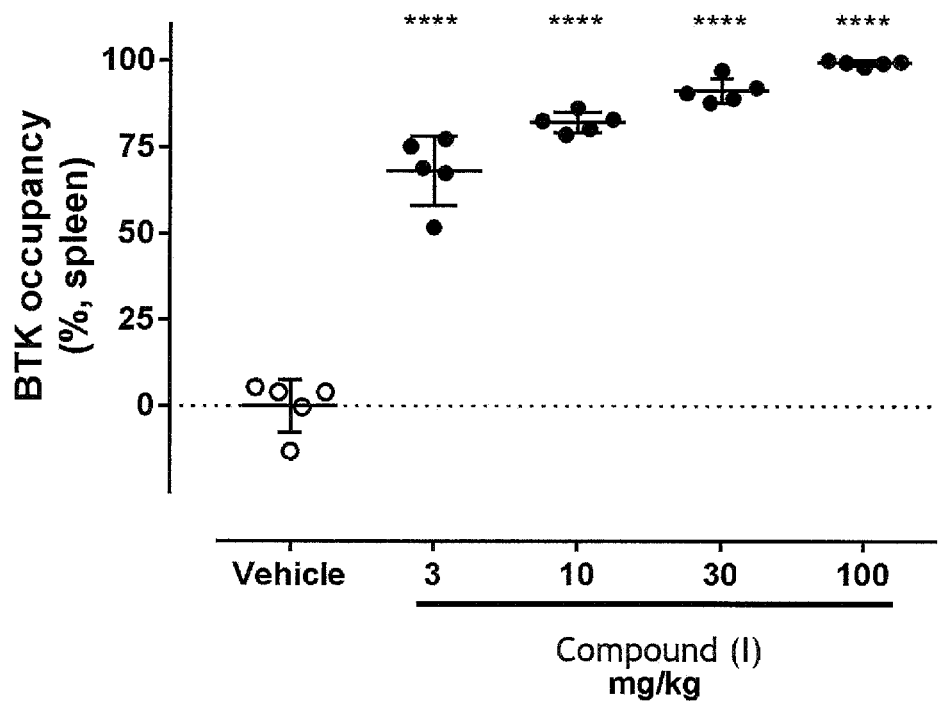
FIG. 2: BTK occupancy in spleen 5 hours after dosing

Oral treatment with compound (I) at a single dose of 3, 10, 30 and 100 mg/kg, given 2 hours prior to induction of the RPA response, reduced skin swelling in a dose-related manner. Maximal effects were seen at 30 and 100 mg/kg (73.0 and 61.2% inhibition, respectively) and partial effects were observed at 3 and 10 mg/kg (22.9 and 29.2% inhibition, respectively) (FIG. 1). BTK occupancy in spleen observed terminally 5 h after the dosing was correlated to efficacy on skin swelling with 68.1% (3 mg/kg), 82.1% (10 mg/kg), 91.3% (30 mg/kg), 99.3% (100 mg/kg). (FIG. 2)

In this model, the inhibition of skin swelling was maximal when compound (I) was dosed 2 hours prior to eliciting the Arthus reaction. The effect diminished gradually and reached baseline when the Arthus reaction was triggered 45 hours or later after compound (I) dosing. This suggests that BTK occupancy in the skin shows a similar time course like spleen, lung and lymph nodes.

Figure 3:
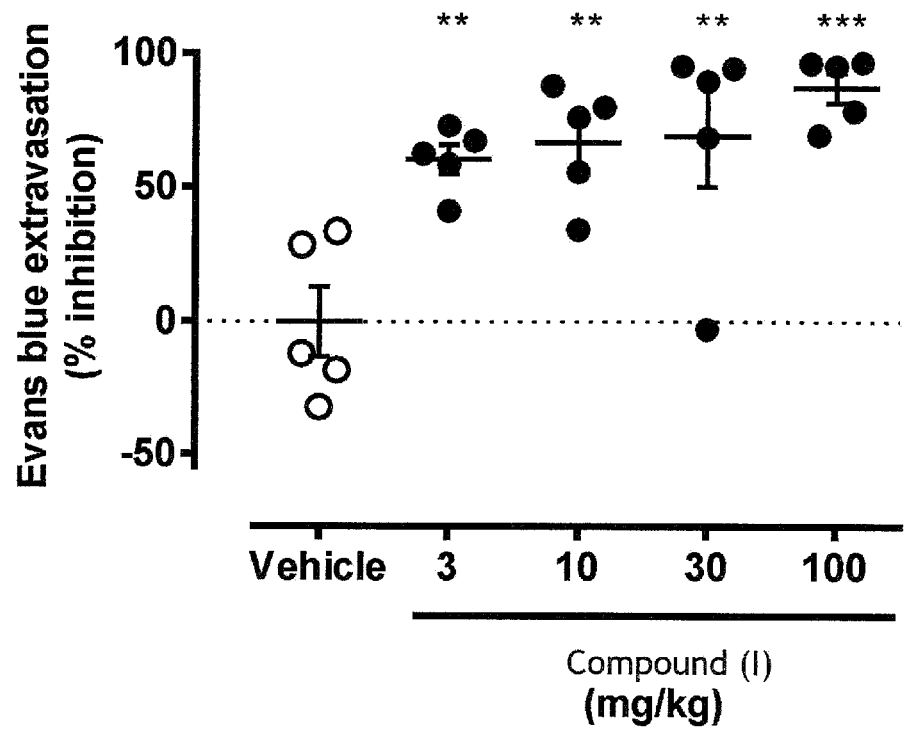
FIG. 3: Compound of Formula (I) inhibits PCA after low-dose IgE sensitization
Figure 4:
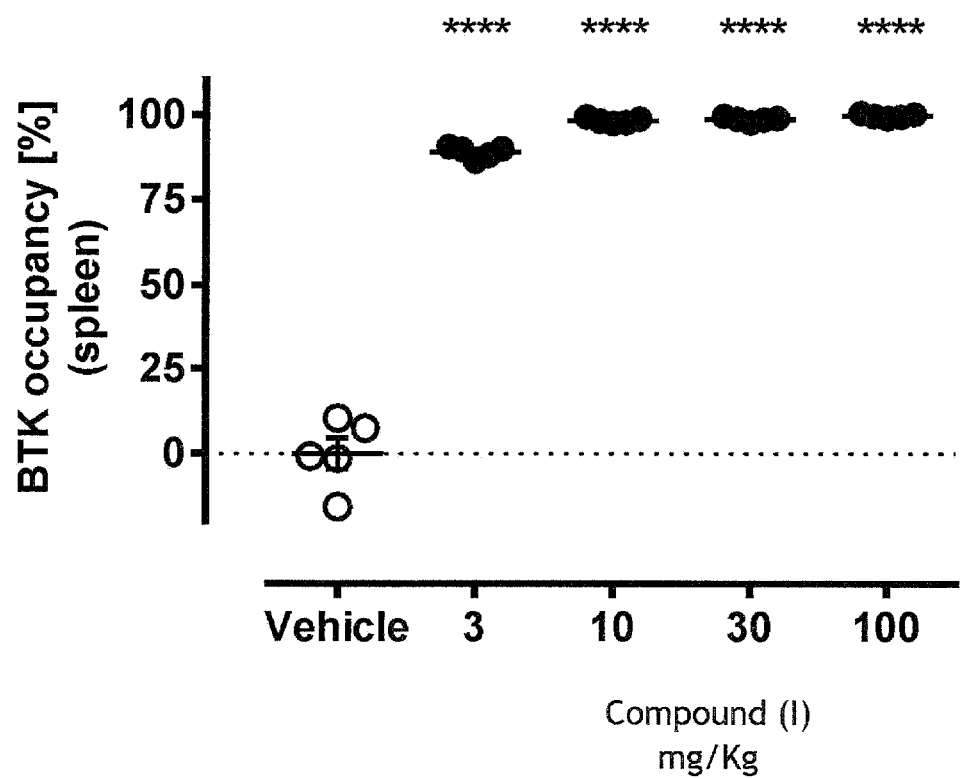
FIG. 4: BTK occupancy in spleen for low-dose IgE senitization

The effects of compound (I) on acute skin hypersensitivity were also assessed after two oral doses of compound (I) in the mouse of model of passive cutaneous anaphylaxis (PCA) (Ovary 1958). The mouse PCA model was used at a low dose of sensitizing IgE antibody to minimize complement-dependent anaphylatoxins (Schafer et al. 2013, The journal of allergy and clinical immunology, 131(2), pp. 541; Hata et al. 1998, Journal of Experimental Medicine, 187(8), pp. 1235). Two oral doses of each 3, 10, 30, or 100 mg/kg compound (I) given 14 and 2 hours before eliciting cutaneous anaphylaxis with hapten showed dose dependent—inhibition of the skin edema measured as Evans blue extravasation. The inhibition of skin edema as measured by Evans blue extravasation ranged from 60.7% (3 mg/kg), 66.9% (10 mg/kg), 69.2% (30 mg/kg), to 87.4% (100 mg/kg). (FIG. 3). Spleen occupancy at 2.5 hours post last dose ranged from 89.1 to 99.7% (representing peak occupancy) (FIG. 4).

The studies in example 1a and 1 b suggest that compound (I) reaches its target in skin and inhibits cutaneous inflammatory reactions efficiently.

In these preclinical pharmacology studies, the BTK occupancy and the respective pharmacologic readouts showed a strong correlation. Thus, BTK occupancy and mast cell-mediated skin hypersensitivity reactions are suitable PD biomarker for use in clinical studies and therefore were used in Phase 1 clinical studies.

Example 2: Phase 1 Clinical Trial

A first-in-human study was conducted to assess the safety and tolerability, pharmacokinetics (PK) and pharmacodynamics (PD) of single and multiple doses of compound (I) both as once daily (qd) and twice daily (bid) oral administration in healthy volunteers and those with atopic diathesis, to support further clinical development of compound (I) in autoimmune diseases. This study also explored the effect of food intake.

First-in-human study in up to approximately 168 healthy volunteers (HVs), of which 64 (in Parts 2 & 4) had asymptomatic atopic diathesis.

Part 1 was a double-blind (subject and investigator blind, sponsor unblinded), placebo-controlled single ascending dose (SAD) escalation study of 10 cohorts (N=80)

Part 2 was a double-blind (subject and investigator blind, sponsor unblinded), placebo-controlled multiple ascending dose (MAD) (13 doses over 12 days) escalation study employing once daily dosing in 6 cohorts in healthy volunteers with asymptomatic atopic diathesis (N=48)

Part 3 was a single dose open-label crossover food effect study in 12 HVs

Part 4 was a double-blind (subject and investigator blind, sponsor unblinded), placebo-controlled multiple dose (25 doses over 12 days) study employing twice daily dosing in 2 cohorts of healthy volunteers with asymptomatic atopic diathesis (N=16)

The SAD part (Part 1) had ten dose levels and the MAD parts (Parts 2 & 4) consisted of eight dose levels (6 cohorts using single daily dosing in Part 2 and 2 cohorts using twice daily dosing in Part 4). Eight subjects were randomized into each cohort to receive either compound (I) or matching placebo in a 6:2 (active: placebo) ratio in the SAD and MAD parts. Within the SAD part, doses up to approximately 4 times the estimated pharmacologically active dose (PAD) were to be evaluated before the MAD part of the study was started, providing there was no safety signal emerging from the SAD part until then. The total daily dose of compound (I) used in Part 2 (MAD qd regimen) and Part 4 (Multiple dose bid regimen) did not exceed the highest SAD dose level explored. Moreover, the total daily dose of Part 4 did not exceed the total daily dose of Part 2.

In Part 1 (SAD) sentinel dosing was to take place for the first administration at each dose level as follows. The first two subjects were dosed on the first day (one with active drug, one with placebo). After a 48-hour observation period the remaining 6 subjects of the cohort (five with active drug, one with placebo) were dosed.

Standard safety monitoring was used throughout all study parts. A dedicated assessment of potential skin bruising events were included. All vital signs, physical examination and subject history, ECGs, adverse events, and laboratory safety parameters (blood chemistry, hematology and urinalysis) up to 96 hours post last dose as well as PK data from the previous dose group (if available) up to 48 hours post last dose were to be reviewed in a blinded fashion for each cohort before dose escalation. Summary safety reports of reported adverse events, clinical safety laboratory parameters, QTc and heart rate were provided after completion of each dose level.

In Parts 1, 2 and 4, each subject participated in a 28-day Screening period (Days −29 to −2), a Baseline period, a Treatment period and a Follow-up period that included an End-of-Study evaluation.

In Part 1, subjects were admitted to the study site on Day −2 or −1 for baseline safety assessments and to confirm eligibility. Eligible subjects received a single dose of compound (I) or placebo under fasting conditions on Day 1.

They were domiciled from Day −1 to the morning of Day 5 (96 hours post last drug administration).

In Parts 2 and 4, subjects were admitted on Day −2 or −1 for baseline safety assessments and to confirm eligibility. Eligible subjects received the first dose of compound (I) under fasting conditions on Day 1, and continued to take study medication under fasting conditions up to and including Day 12. Subjects were domiciled from Day −2 or −1 until the morning of Day 16, which equals 96 hours after the last dose of compound (I) was received. In Parts 2 and 4, the study medication was given once daily and twice daily respectively (details are found in the schedule of assessments).

Part 3 was an open-label, randomized, two-way cross-over, single dose study to assess food effects. In Part 3, each subject participated in a 28 day screening period (Day −29 to −2), 2 baseline (Day −1) and 2 treatment periods, each consisting of a single dose administration on Day 1 followed by safety and PK assessment up to Day 5. Treatment period 2 consisted of a follow-up visit and an end of study evaluation on Day 22 and 40, respectively. The two treatment periods were separated by a wash-out period of at least 18 days (+1-1 day).

2. Subjects were required to weigh at least 50 kg with a body mass index (BMI) within the range of 18-30 kg/m2 (inclusive). BMI=body weight (kg)/[Height (m)]$^2$.
3. At screening, and first baseline, vital signs (body temperature, systolic and diastolic blood pressure and pulse rate) were assessed in the sitting position after the subject has rested for at least 3 minutes and again (when required) after 3 minutes in the standing position. Sitting vital signs were required to be within the following ranges (inclusive):
   Oral body temperature between 35.0-37.5° C.
   Systolic blood pressure 90-139 mm Hg
   Diastolic blood pressure 50-89 mm Hg
   Pulse rate 50-90 bpm Key Exclusion Criteria
1. History of hypersensitivity to any of the study drugs or to drugs of similar chemical classes.
2. History of clinically significant ECG abnormalities, or any of the following ECG abnormalities at screening and/or pre-treatment:
   PR interval>200 msec
   QRS complex>120 msec

| Objective | Endpoint |
|---|---|
| Primamary objectives | |
| All Parts: To assess the safety and tolerability of single and multiple ascending oral doses of compound (I) | All safety assessments including physical examination and anamnesis, vital signs, ECG, safety laboratory, AEs, and SAEs. Included a designated evaluation of the occurrence of skin bruising. |
| Secondary objectives | |
| Parts 1 2 & 4: to assess the blood PK of single and multiple doses of compound (I) in healthy volunteers and atopic subjects. | Single and multiple dose PK parameters such as Cmax, Tmax, AUCinf, AUClast, AUCtau, T1/2, MRT, Racc, Vz/F and Cl/F. |
| Part 3: to assess the blood PK of a single dose of compound (I) under fed and fasted conditions in healthy volunteers. | Single dose PK parameters: Cmax, Tmax, AUClast, AUCinf, T1/2, MRT, Vz/F and CL/F. |
| Exploratory objectives | |
| Parts 1, 2 & 4: to explore urine PK (Part 2 & 4) and PD of single and multiple doses of compound (I). | BTK occupancy in peripheral blood Skin prick test responses to a known allergen (Part 2 & 4) ex vivo cellular PD biomarkers that provided additional measures of drug response to compound (I) by inhibition of peripheral blood basophil degranulation (FcεR-induced CD63 and CD203 cexpression) |
| All Parts: to describe the concentration effect relationship with PD markers (e.g. BTK occupancy, ex vivo cellular PD biomarkers) and characterize nonlinearities in PK (if any) using population PK-PD models | Population model PK parameters (e.g., CL/F, V/F and Ka) and PD model parameters (e.g., irreversible binding constant Kirr) and their associated intra and inter-individual variability (CV%) |

Key Inclusion Criteria:
1. Male and female healthy subjects with an age range between 18 and 65 years (inclusive), and in good health as determined by past medical history, physical examination, vital signs, electrocardiogram, and laboratory tests at screening. Healthy subjects participated in Part 2 or Part 4 with atopic diathesis as per eligibility for these specific study portions. Atopic healthy volunteers had to have a positive skin prick test to a known allergen at screening (atopic diathesis) but were clinically asymptomatic and did not require any systemic medication.

QTcF>450 msec (males)
   QTcF>460 msec (females)
3. Hemoglobin levels below 12.0 g/dL at screening or first baseline.
4. Platelet count outside of the normal range (below 150×10$^9$/L or above 450×10$^9$) at screening or first baseline.
5. Any clinically significant abnormalities in any of the standard coagulation tests including the prothrombin time (PT), partial thromboplastin time (PTT), or International Normalized Ratio (INR) at screening and/or baseline.

6. History or presence of thrombotic or thromboembolic event, or increased risk for thrombotic or thromboembolic event.

Treatments Administered

Part 1 (SAD)

Subjects were assigned to one of the following 10 cohorts. In each cohort, 8 subjects were randomized to either compound (I) or matching placebo in an overall 6:2 ratio. The first sub-cohort was randomized in a 1:1 ratio as one subject on compound (I) and one on matching placebo. The remaining 6 subjects per cohort, dosed after a 48-hour observation period of the initially dosed 2 subjects, were randomized in a 5:1 ratio.

Cohort 1: single oral dose of 0.5 mg compound (I) or matching placebo

Cohort 2: single oral dose of 1.5 mg compound (I) or matching placebo

Cohort 3: single oral dose of 5 mg compound (I) or matching placebo

Cohort 4: single oral dose of 15 mg compound (I) or matching placebo

Cohort 5: single oral dose of 30 mg compound (I) or matching placebo

Cohort 6: single oral dose of 60 mg compound (I) or matching placebo

Cohort 7: single oral dose of 100 mg compound (I) or matching placebo

Cohort 8: single oral dose of 200 mg compound (I) or matching placebo

Cohort 9: single oral dose of 400 mg compound (I) or matching placebo

Cohort 10: single oral dose of 600 mg compound (I) or matching placebo

Part 2 (MAD, qd Regimen)

Subjects were assigned to one of the following 6 cohorts. In each cohort, 8 subjects were randomized to either compound (I) or matching placebo in a 6:2 ratio.

Cohort 1: multiple oral doses of 10 mg compound (I) or matching placebo

Cohort 2: multiple oral doses of 25 mg compound (I) or matching placebo

Cohort 3: multiple oral doses of 50 mg compound (I) or matching placebo

Cohort 4: multiple oral doses of 100 mg compound (I) or matching placebo

Cohort 5: multiple oral doses of 400 mg compound (I) or matching placebo

Cohort 6: multiple oral doses of up to 600 mg compound (I) or matching placebo

Part 3 (Food Effect)

Subjects were randomized to one of the 2 treatment sequences (Table 9) in the ratio of 1:1. Definition of treatment sequences for Part 3

| Sequence | Period 1 | Period 2 |
|---|---|---|
| 1 | Compound (I) (60 mg) Fasted | Compound (I) (60 mg) Fed |
| 2 | Compound (I) (60 mg) Fed | Compound (I) (60 mg) Fasted |

Part 4 (MAD, Bid Regimen)

Subjects were assigned to one of the following cohorts. In each cohort, 8 subjects were randomized to either Compound (I) or matching placebo in a 6:2 ratio.

Cohort 1: multiple oral doses of 100 mg Compound (I) or matching placebo in a bid regimen Cohort 2: multiple oral doses of 200 mg Compound (I) or matching placebo in a bid regimen Pharmacokinetics Data Bioanalytical Methods:

Pharmacokinetic samples were obtained in blood and evaluated in all subjects at all dose levels. The samples from placebo subjects were not analyzed. The samples for PK assessments from subjects were collected at time points defined in the study. Compound (I) concentrations were determined in blood by a validated LC-MS/MS method.

Figure 5:
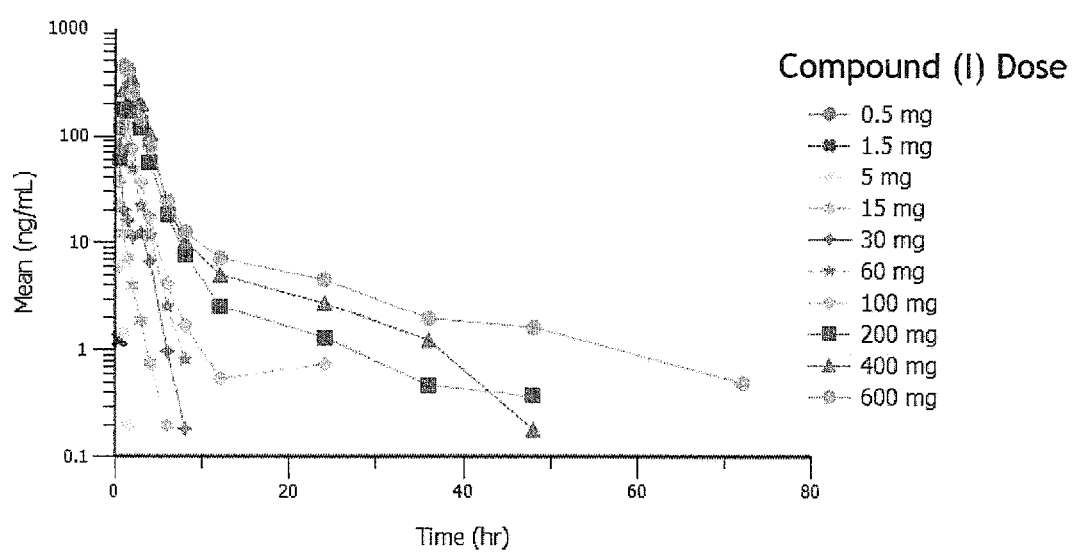
FIG. 5: Blood concentration—time course of compound (I) after single ascending doses 0.5 mg-600 mg

Single Ascending Doses of 0.5 mg-600 mg Pharmacokinetics:

Mean blood concentration—time course of compound (I) after single ascending doses are shown in FIG. 5.

Compound (I) was rapidly absorbed with time to reach Cmax of about 1-1.5 hr across all doses. The absorption phase was characterized by a single distinct absorption peak in most subjects. Drug disposition displayed a bi-exponential decline. Most of the drug was eliminated under the initial distribution phase suggesting substantial drug clearance may occur prior to reaching whole-body tissue equilibrium. The apparent terminal elimination phase was not reached until 12 hours post dose and was measurable only in subjects receiving doses of 100 mg and above. Measureable terminal half-lives ranged from 4 hr (100 mg) up to 18 hr (600 mg) leading to a mean residence time (MRT) in the circulation of 1 h up to 5 hours (MRT≈T1/2/ln2). The distribution phase demonstrated a dominant dose-independent T1/2 of ~1 h. The calculated geometric mean of oral blood clearance after single dose administration (CL/F) ranged from 250 to 506 L/h across SAD cohorts, with an estimate of about 383 L/h across all cohorts.

Multiple Oral Dose Pharmacokinetics

Figure 6:
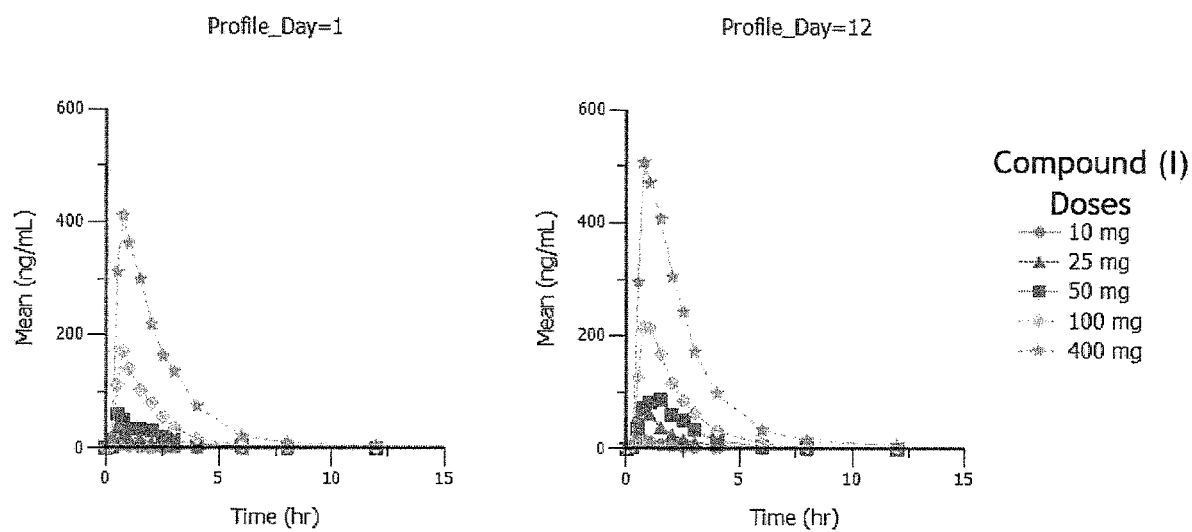
FIG. 6: Blood concentration—time course of compound (I) after multiple ascending doses of 10 mg-400 mg, q.d. dosing

Mean blood concentration—time course of compound (I) after multiple ascending doses of 10 mg-400 mg are shown in FIG. 6.

Geometric mean apparent clearance at steady-state after oral dosing (CLss/F, Day 12 MAD, q.d.) ranged between 246 L/h to 414 L/h across cohorts. In general a lower clearance was observed at steady state when compared to day 1 but this difference almost disappeared at doses of 100 mg and above (Tables 8-1 (day 1) and table 8-2 (day 12)). The reason for this behavior is likely the covalent target (BTK) binding contributing to the initial clearance of compound (I). This effect is most prominent at day 1 as on consecutive days the remaining target occupancy at trough reduces the fractional contribution of target binding to the clearance (CLss/F). Naturally, this difference decreases with increase in the dose when target occupancy at trough is near complete. Consequently, drug exposure (AUC, Cmax) was found to be higher on day 12 compared to day 1, as illustrated by the (within-subject) drug accumulation ratio (Racc), which ranged between 5 (low dose) to 1.2 (high dose) and was generally higher for AUC than Cmax, confirming that an effect on systemic clearance may be involved.

TABLE 8-1

Summary of PK parameters of compound (I) at multiple ascending doses of 10-600 mg, q.d. dosing
Analyte: compound of Formula (I), Matrix: Blood and Urine
Profile: Day 1

| PK parameter (unit) | Compound of Formula (I) | | | | | |
|---|---|---|---|---|---|---|
| | 10 mg qd N = 6 | 25 mg qd N = 6 | 50 mg qd N = 6 | 100 mg qd N = 6 | 400 mg qd N = 6 | 600 mg qd N = 6 |
| Cmax (ng/mL) | 8.40 ± 2.02 (24.1) 8.03 (6.36-11.4) [6] | 40.9 ± 21.6 (52.9) 37.3 (14.1-80.4) [6] | 76.5 ± 22.0 (28.8) 70.1 (47.3-107) [6] | 187 ± 85.0 (45.4) 189 (75.6-285) [6] | 518 ± 89.1 (17.2) 513 (383-622) [6] | 550 ± 87.6 (15.9) 545 (461-691) [6] |
| Tmax (h) | 0.517 (0.500-1.00) [6] | 0.875 (0.283-1.50) [6] | 0.500 (0.483-2.00) [6] | 0.742 (0.500-1.95) [6] | 0.750 (0.500-1.50) [6] | 0.750 (0.500-3.00) [6] |
| AUClast (h * ng/mL) | 4.17 ± 1.38 (33.0) 4.40 (1.79-5.62) [6] | 43.9 ± 24.6 (56.2) 45.5 (15.3-78.5) [6] | 113 ± 34.2 (30.3) 103 (81.9-154) [6] | 311 ± 89.1 (28.6) 333 (168-416) [6] | 973 ± 379 (39.0) 826 (694-1720) [6] | 1080 ± 377 (35.1) 931 (699-1700) [6] |
| AUC0-24 (h * ng/mL) | 4.94 ± 1.35 (27.2) 4.94 (3.99-5.89) [2] | 44.9 ± 25.2 (56.0) 46.6 (15.6-79.7) [6] | 116 ± 32.9 (28.4) 107 (84.0-155) [6] | 315 ± 91.5 (29.0) 338 (168-419) [6] | 977 ± 378 (38.7) 826 (702-1720) [6] | 1080 ± 377 (35.0) 932 (700-1700) [6] |
| MRT (h) | 0.761 ± 0.151 (19.8) 0.766 (0.548-0.956) [6] | 1.18 ± 0.490 (41.6) 1.17 (0.460-1.87) [6] | 2.53 ± 1.17 (46.4) 2.44 (1.17-4.65) [6] | 2.79 ± 1.28 (45.7) 2.16 (1.65-4.62) [6] | 3.02 ± 1.11 (36.8) 2.94 (1.64-4.98) [6] | 3.14 ± 0.580 (18.5) 3.22 (2.31-3.96) [6] |

Statistics are Mean ± SD (CV %)
Median (Min-Max) [n]
CV % = Coefficient of variation (%) = SD/Mean * 100
For Tmax and T½, only Median (Min-Max) [n] are presented

TABLE 8-2

Analyte: Compound of Formula (I), Matrix: Blood and Urine
Profile: Day 12

| PK parameter (unit) | Compound of Formula (I) | | | | | |
|---|---|---|---|---|---|---|
| | 10 mg qd N = 6 | 25 mg qd N = 6 | 50 mg qd N = 6 | 100 mg qd N = 6 | 400 mg qd N = 6 | 600 mg qd N = 6 |
| Cmax (ng/mL) | 18.2 ± 5.90 (32.4) 17.2 (11.8-26.4) [6] | 85.9 ± 31.5 (36.6) 78.4 (43.9-126) [6] | 102 ± 22.0 (21.6) 100 (73.3-131) [6] | 233 ± 84.1 (36.1) 205 (167-386) [6] | 551 ± 263 (47.7) 476 (260-928) [6] | 563 ± 229 (40.6) 475 (377-985) [6] |
| Tmax (h) | 0.625 (0.500-1.00) [6] | 0.750 (0.500-1.00) [6] | 1.00 (0.533-1.50) [6] | 0.867 (0.733-1.50) [6] | 0.758 (0.700-1.50) [6] | 0.883 (0.500-3.00) [6] |
| AUClast (h * ng/mL) | 22.9 ± 3.50 (15.3) 22.4 (18.3-28.2) [6] | 114 ± 59.7 (52.3) 98.2 (30.1-190) [6] | 207 ± 80.4 (38.9) 179 (126-323) [6] | 488 ± 172 (35.3) 444 (336-770) [6] | 1300 ± 602 (46.3) 1180 (650-2310) [6] | 1240 ± 341 (27.5) 1070 (953-1740) [6] |
| AUCinf (h * ng/mL) | 24.7 ± 3.65 (14.8) 24.3 (19.6-29.9) [6] | 117 ± 60.4 (51.5) 102 (31.7-194) [6] | 209 ± 80.0 (38.2) 181 (127-325) [6] | 577 ± 207 (35.9) 595 (361-774) [3] | 1330 ± 608 (45.8) 1210 (665-2330) [6] | 1260 ± 338 (26.8) 1090 (994-1760) [6] |
| AUC0-24 (h * ng/mL) | 24.0 ± 3.60 (15.0) 23.6 (18.9-29.3) [6] | 117 ± 60.9 (52.2) 101 (30.9-194) [6] | 209 ± 80.2 (38.4) 181 (127-325) [6] | 485 ± 179 (36.9) 429 (336-774) [6] | 1280 ± 577 (45.3) 1140 (677-2270) [6] | 1230 ± 356 (29.0) 1060 (908-1740) [6] |
| T½ (h) | 0.961 (0.667-1.21) [6] | 1.15 (0.680-1.33) [6] | 1.15 (0.813-1.55) [6] | 1.41 (1.41-11.9) [3] | 8.51 (1.22-22.3) [6] | 8.29 (4.69-17.3) [6] |
| Vss/F (L) | 554 ± 90.4 (16.3) 562 (407-657) [6] | 407 ± 208 (51.1) 334 (247-793) [6] | 431 ± 172 (40.0) 346 (313-751) [6] | 1910 ± 2780 (145.9) 338 (264-5120) [3] | 4400 ± 3340 (75.8) 3440 (624-8820) [6] | 7130 ± 5120 (71.9) 7070 (2340-16500) [6] |
| CLss/F (L/h) | 425 ± 64.8 (15.3) 423 (341-529) [6] | 307 ± 253 (82.5) 248 (129-809) [6] | 268 ± 92.8 (34.6) 276 (154-395) [6] | 198 ± 88.7 (44.8) 166 (129-298) [3] | 366 ± 150 (41.0) 351 (177-591) [6] | 521 ± 131 (25.1) 569 (345-661) [6] |

TABLE 8-2-continued

Analyte: Compound of Formula (I), Matrix: Blood and Urine
Profile: Day 12

| PK parameter (unit) | Compound of Formula (I) | | | | | |
|---|---|---|---|---|---|---|
| | 10 mg qd N = 6 | 25 mg qd N = 6 | 50 mg qd N = 6 | 100 mg qd N = 6 | 400 mg qd N = 6 | 600 mg qd N = 6 |
| T½, acc | 1.00 (1.00-1.00) [6] | 1.00 (1.00-1.00) [6] | 1.00 (1.00-1.00) [6] | 1.01 (1.00-1.73) [6] | 1.18 (1.00-1.90) [6] | 1.16 (1.03-1.62) [6] |
| Amount recovered (mg) | 0.0663 ± 0.0309 (46.5) 0.0630 (0.0346-0.109) [6] | 0.114 ± 0.0706 (62.0) 0.126 (0.0326-0.217) [6] | 0.233 ± 0.0880 (37.7) 0.185 (0.165-0.378) [5] | 0.648 ± 0.330 (50.9) 0.561 (0.305-1.12) [6] | 1.25 ± 0.647 (51.7) 1.12 (0.547-2.37) [6] | 1.54 ± 0.915 (59.3) 1.43 (0.528-3.03) [6] |
| Amount recovered (%) | 0.663 ± 0.309 (46.5) 0.630 (0.346-1.09) [6] | 0.456 ± 0.283 (62.0) 0.502 (0.130-0.868) [6] | 0.467 ± 0.176 (37.7) 0.370 (0.331-0.757) [5] | 0.648 ± 0.330 (50.9) 0.561 (0.305-1.12) [6] | 0.313 ± 0.162 (51.7) 0.280 (0.137-0.593) [6] | 0.257 ± 0.153 (59.3) 0.238 (0.0880-0.506) [6] |
| Renal clearance (mL/min) | 45.3 ± 18.0 (39.8) 41.6 (24.4-70.3) [6] | 16.8 ± 6.81 (40.5) 18.9 (5.43-24.3) [6] | 20.4 ± 2.40 (11.7) 20.5 (17.1-23.4) [5] | 21.6 ± 5.41 (25.1) 21.1 (14.6-30.9) [6] | 16.9 ± 7.13 (42.3) 14.5 (11.5-30.7) [6] | 20.0 ± 8.25 (41.2) 18.1 (8.98-30.3) [6] |

Statistics are Mean ± SD (CV %)
Median (Min-Max) [n]
CV % = Coefficient of variation (%) = SD/Mean * 100
For Tmax and T½, only Median (Min-Max) [n] are presented In general, blood concentrations at 24 hours post last dose were typically below 1 ng/ml, except for a few subjects at 100 mg and above indicating near-complete washout of compound (I) within two consecutive doses. The latter also suggests that steady state is reached within a few doses.

Figure 7:
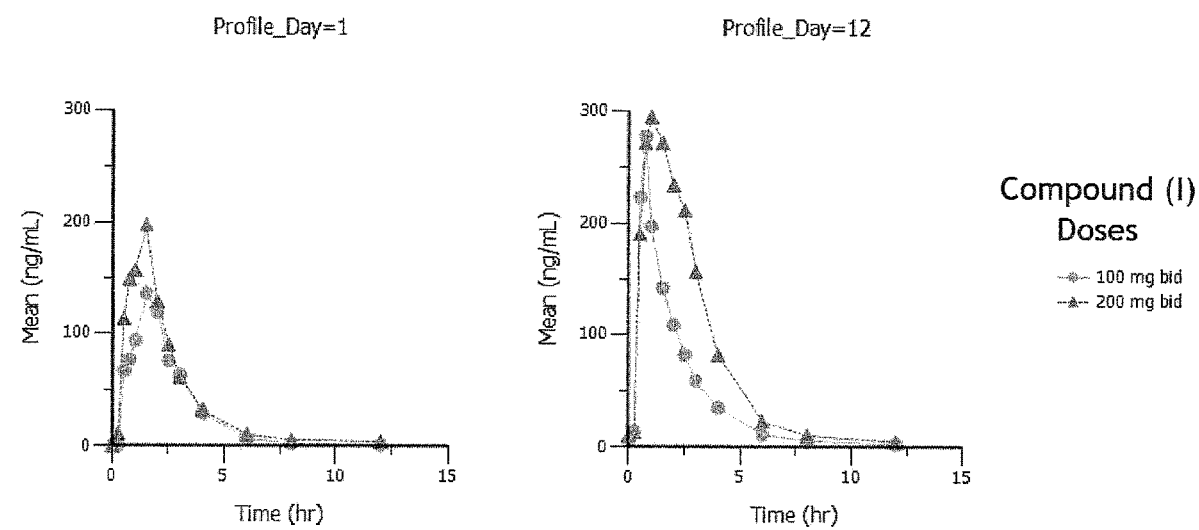
FIG. 7: Blood concentration—time course of compound (I) after multiple ascending doses of 100 mg b.i.d. and 200 mg b.i.d.

Due to the higher turnover of BTK in tissues, b.i.d. dosing was also investigated. Mean blood concentration time profiles obtained after multiple ascending twice daily doses of 100 mg and 200 mg are shown in FIG. 7. In line with results from other cohorts, a fast absorption with a Tmax of around 1 h was observed for doses after b.i.d. regimen. The observed accumulation factor (Racc) amounted to 1.5 (100 mg) and 2.0 (200 mg) for AUC and about 1.65 for Cmax (both doses). A dose proportional increase of AUCtau was observed at day 12 while only slight increase (1.33-fold) was found for Cmax. In conclusion, b.i.d dosing of compound (I) provides an option to address the faster target resynthesis in tissues during the dosing interval without compromising the overall PK profile and the need for high dose q.d. treatment.

Figure 8:
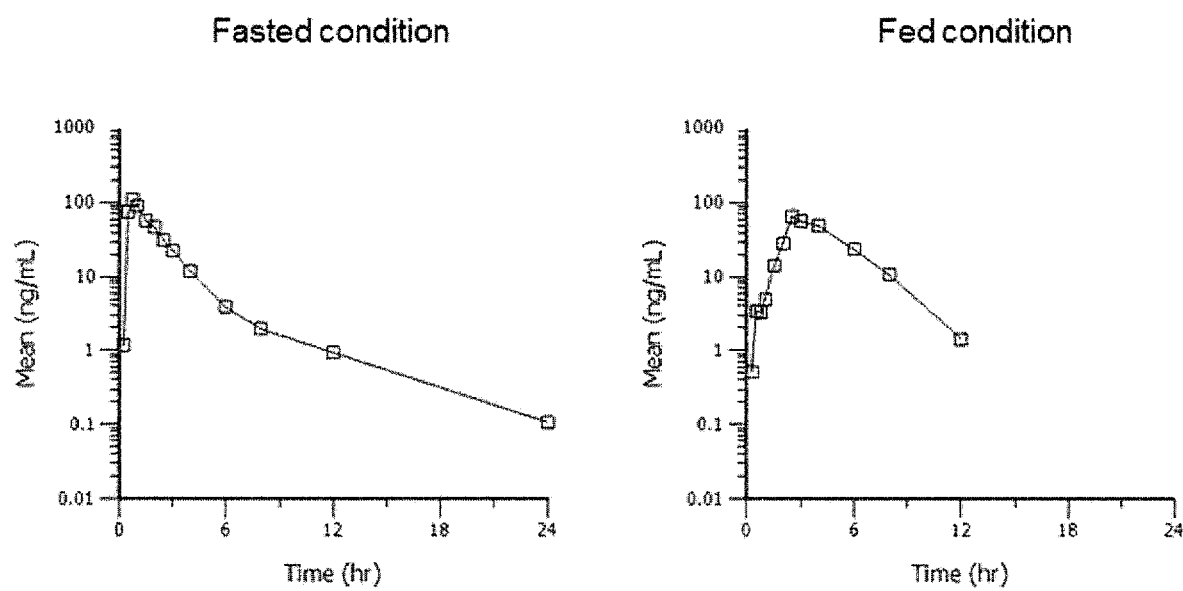
FIG. 8: Food effect as observed after a single oral dose of 60 mg of compound of Formula (I)

Food Effect: Result Part 3:

The PK data from the food effect cohort summarized in Table 9 below indicated a lower absorption rate as suggested by a 1.25-fold lower Cmax and a more complete overall absorption as indicated by a 1.4-fold higher AUC0-24. Most importantly the mean $T_{max}$ was shifted from 1 hr (fasted) to >3 hr (fed). (FIG. 8)

TABLE 9

Summary of PK parameters: Food effect compound (I) after a single dose of 60 mg

| Condition | Variable | Mean | SD | Min | Max | GeoMean | CV % GeoMean |
|---|---|---|---|---|---|---|---|
| FAST | AUC0-24 | 202.29 | 94.28 | 70.40 | 407.26 | 182.08 | 52.66 |
| | AUClast | 196.49 | 91.45 | 69.21 | 399.64 | 177.17 | 52.01 |
| | Cmax | 114.81 | 57.97 | 33.90 | 252.00 | 100.95 | 60.40 |
| | Tlast | 10.50 | 4.98 | 6.00 | 24.00 | 9.66 | 42.80 |
| | Tmax | 1.02 | 0.47 | 0.75 | 2.00 | 0.95 | 38.32 |
| FED | AUC0-24 | 263.89 | 91.56 | 132.79 | 426.96 | 248.51 | 38.46 |
| | AUClast | 251.96 | 85.43 | 130.60 | 396.42 | 237.84 | 37.69 |
| | Cmax | 83.39 | 21.41 | 52.10 | 126.00 | 80.86 | 26.64 |
| | Tlast | 9.50 | 2.28 | 6.00 | 12.00 | 9.25 | 24.72 |
| | Tmax | 3.42 | 1.41 | 2.00 | 6.00 | 3.18 | 39.95 |

Units: AUC (ng*hr/mL);
Cmax (ng/mL);
T (hr)
CV (Coefficient variation (%) = SD/Mean * 100

Pharmacodynamics

Pharmacodynamics (PD) was characterized by assessing target occupancy and distal pathway inhibition. Measurements of BTK occupancy in human whole blood (derived as ratio of free and total BTK), served as direct marker of therapeutic target engagement.

The relationship between BTK occupancy, dose, systemic compound exposure and efficacy on complex in vivo pathway and disease readouts has been established across preclinical models for compound of Formula (I). (e.g. Example 1)

Compound of formula (I) is an irreversible inhibitor of BTK, the extent and duration of BTK occupancy were determined. The PD effect of compound (I) was assessed by measuring both free BTK (not bound) and total BTK in whole blood by enzyme-linked immunosorbent assay (ELISA) on Meso Scale Diagnostics (MSD) platform in two separate assays.

The relationship between dose and pharmacodynamics was characterized by measurements of BTK occupancy in human blood (derived as ratio of free and total BTK), a direct marker of therapeutic target engagement. BTK occupancy was determined for single ascending doses ranging 0.5 to 400 mg, for q.d. multiple ascending doses ranging from of 10 mg and 400 mg, and for b.i.d. multiple ascending doses of 100 mg and 200 mg.

Compound of Formula (I) exhibited a clear dose-dependent increase in both extent and duration of peripheral blood BTK occupancy. Peak target occupancy was generally seen as early as 0.5 h post dose, indicating rapid onset with no relevant hysteresis in drug effect relative to peak drug exposure. As concluded from its ability to bind BTK covalently, target occupancy was sustained well beyond its disposition from the systemic circulation, indicating a non-equilibrium PK-PD relationship. Accordingly, duration of BTK occupancy is concluded to be governed by the rate of de novo synthesis of BTK.

Figure 9:
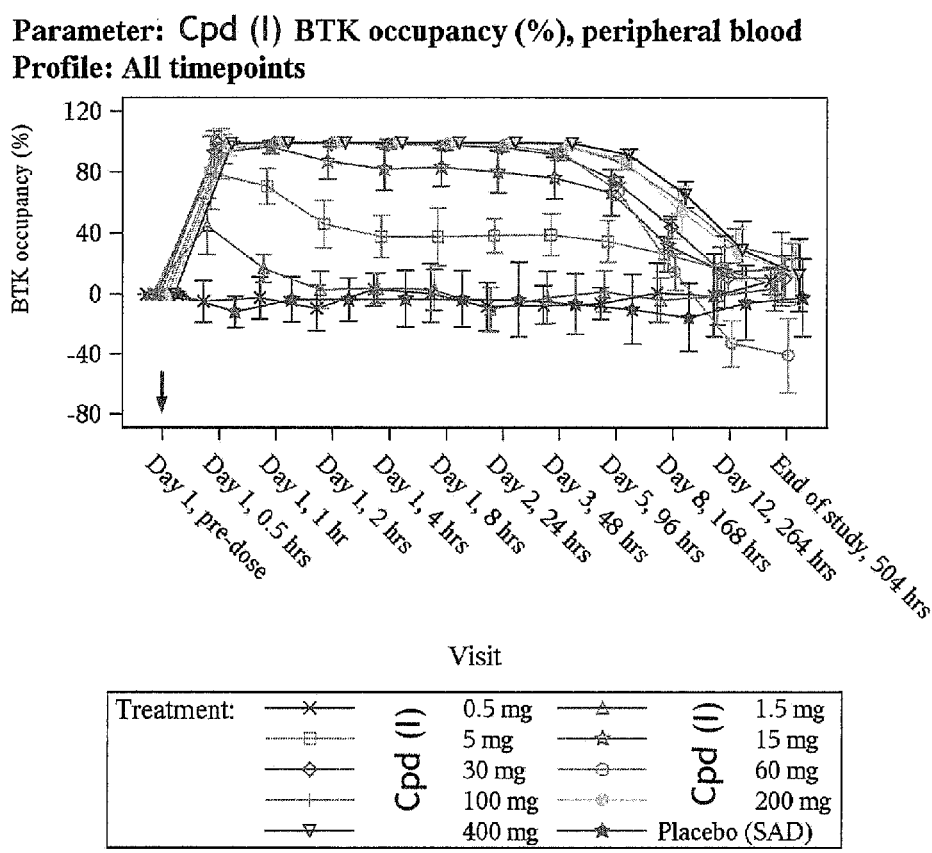
FIG. 9: Arithmetic mean (SD) percent BTK occupancy in peripheral blood after a single dose of Compound of Formula (I)

Unlike the lower dose cohorts (0.5-1.5 mg), single doses of 15 mg compound (I) and above established a peak target occupancy approaching 100% in nearly all subjects, which remained above 80% at 24 h. While the response varied greatly among subjects at 15 mg, doses of 30 mg and higher conveyed sustained (>24 h) and near-complete (>90%) occupancy in all subjects, with clearly reduced between-subject variability. Time to refresh BTK protein pool to pre-dose levels was about 10 days, corresponding to median turnover T1/2 of about 48 hours (FIG. 9).

After multiple doses of compound (I), already 10 mg compound (I) q.d achieved >96% through BTK occupancy in blood pre-dose at day 12.

In addition, ex vivo inhibition of basophil activation (monitored by surface expression of CD63 and CD203c) was used as distal mechanistic biomarker to test downstream PD effects of compound (I). To determine the PD effect of compound (I) on basophil activation, whole blood was stimulated ex vivo with anti-IgE. Degranulation was evaluated by percentage of CD63+ and CD203+ basophils by flow cytometry.

After single ascending doses of compound (I), data indicate a dose-dependent inhibition of FcεR1-mediated basophil activation. Ex-vivo blood basophil activation as measured by CD63 was near-completely inhibited (>89%) at doses of 60 mg and reached close to a 100% inhibition at higher doses 24 h post dose. In contrast, maximum inhibition of CD203c 24 h after a single dose of compound (I) (appr. 50% inhibition) was only achieved with 200 mg compound (I).

Figure 10:
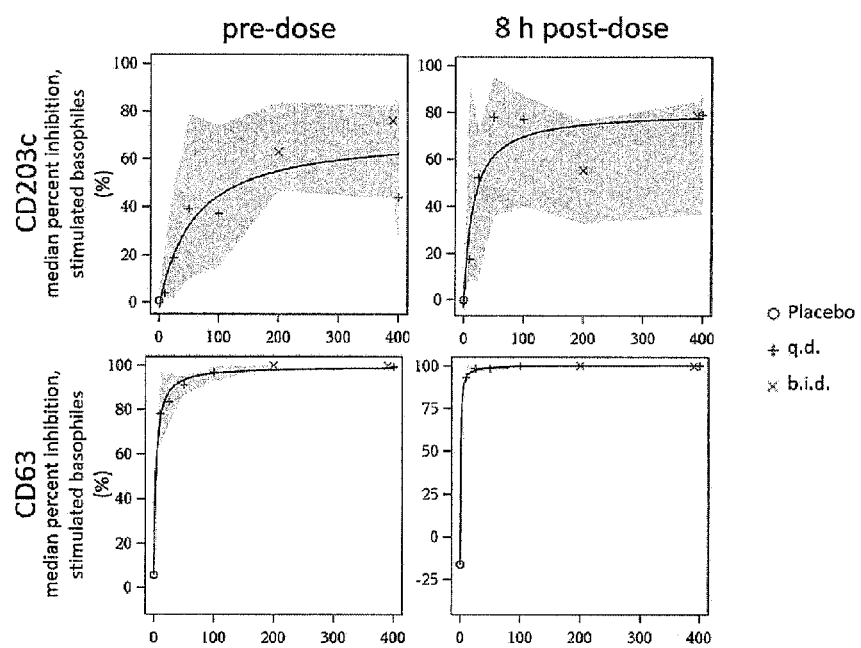
FIG. 10: Median percent inhibition of basophil activation versus total daily dose of Compound of Formula (I) at day 12 of multiple ascending doses of Compound of Formula (I)

At day 12, 8 h after q.d. or b.i.d. administration of MAD of compound of Formula (I), already the lowest tested dose of compound (I) (10 mg q.d.) resulted in >90% inhibition of CD63 upregulation and trough level inhibition of CD63 is >90% at compound (I) doses ≥50 mg q.d. (FIG. 10). Maximum trough inhibition of CD203c activation at Day 12 was consistently higher than after a single dose of compound (I) and was only achieved with b.i.d. administration of 100 mg and 200 mg compound (I).

The ability of compound (I) to inhibit a defined allergen response has been evaluated by means of the skin prick test (SPT) in healthy atopic subjects in the MAD study part of the first in human study. SPT was performed prior to dosing (at screening, baseline and pre-dose on Day 1) and at different time points after the first dose (Day 1) and after 11 days of once daily dosing (Day 12).

Figure 11:
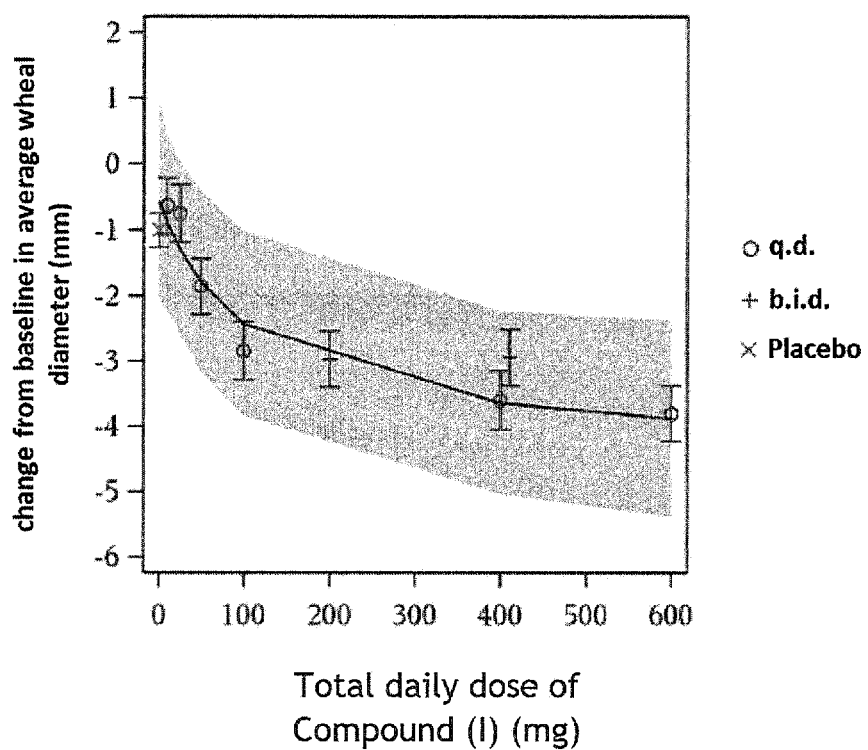
FIG. 11: Reduction of whealsize in-skin prick test in multiple ascending dose

Similar to the inhibition of ex vivo basophil activation, a dose-dependent effect on wheal diameter was discernable in multiple ascending dose cohorts as indicated by the reduction of average post-dose wheal size compared to baseline (FIG. 11). The effect started to plateau at around 100 mg compound (I) q.d.

Rationale for Dose Selection/Conclusion

Healthy volunteers have been exposed to compound (I) in phase 1 clinical studies with doses ranged from 0.5 mg to 600 mg either given as a single dose or given up to 18 days once or twice daily. Compound (I) was well tolerated and there was no serious or severe adverse event related to compound (I) intake. In the clinical study, observed adverse events (AEs) did not appear to be dose-dependent, the majority were single events, and were generally mild in nature. Thus, clinical safety information support the doses selected for this Phase 2b study.

The dose-levels of this invention were derived from the following analyses (BTK occupancy, inhibition of basophil activation (monitored by CD63 and CD203c up-regulation) in healthy volunteers; and impact on skin prick tests (SPT) in asymptomatic atopic healthy volunteers—a proxy for mast cell and basophil inhibition within the skin.

In this above described clinical trial, administration of 10 mg of compound (I) q.d. resulted in nearly complete BTK occupancy in blood, >90% reduction of CD63 up-regulation (8 h after administration of COMPOUND (I) in steady state), and minimal inhibition of wheal size in SPT. 10 mg of compound (I) q.d. therefore corresponds to the onset of biological activity. At 100 mg of compound of Formula (I), mean reduction of wheal size in SPT started to plateau. Therefore, 100 mg of the compound corresponds to the maximal effect of COMPOUND (I). A middle dose of thirty-five mg compound (I) q.d. is well suited to accurately describe the dose-response curve of COMPOUND (I) q.d.

Compound of Formula (I) inhibits BTK by covalent binding. While BTK occupancy in blood is >24 hours (h), fast BTK turnover in tissue (example given approximately 5 hours in the spleen of rodents) may require b.i.d. administration of compound (I) to reach maximal efficacy. Doses of 10 mg, 25 mg and 100 mg compound (I) b.i.d., respectively, accurately describe the dose-response curves of compound (I) when given twice a day.

Safety in Humans

For the analysis of adverse effects, the Placebo subjects from all SAD and MAD cohorts (2 per cohort) and separated by the SAD and MAD parts were pooled into one Placebo group (n=20 for SAD and n=16 for MAD) to be compared with each single compound (I) dose group (n=6 each) and the total compound (I) group (n=60 for SAD and n=48 for MAD). There were no apparent major differences in the demographic data between placebo and the active groups both for the SAD and MAD populations. Safety assessment of the FIH study in healthy volunteers does not reveal significant safety concerns at dosing up to 600 mg.

Example 3: Efficacy and Safety Data in CSU Patients Who Remain Symptomatic Despite Treatment with Standard Care A Phase 2b is conducted as a multicenter, randomized, double-blind, parallel-group, placebo-controlled study in order to investigate the safety, tolerability, and efficacy of six dosing groups of orally administered compound of Formula (I) in subjects with inadequately controlled CSU despite treatment with (second generation) H1-antihistamine treatment.

Throughout the study (i. e. Day −14 until Day 113), subjects are on a stable treatment regimen with a second generation H1-antihistamine at a locally approved licensed posology ("background medication").

Subjects may take an additional second generation H1-antihistamine that is eliminated primarily via renal excretion (eg cetirizine, levocetirizine or bilastine) as rescue medication. The rescue H1-antihistamine must differ from the background H1-antihistamine and may only be administered to treat unbearable symptoms (itch) of CSU on a day-to-day basis throughout the study (from Day −14 until Day 113).

All other CSU therapies (including H1-antihistamines at higher than approved doses) are prohibited (see Table 10)

The outlines of the study design includes three periods:
Screening period (10-14 days prior to randomization): During the screening period, subjects who have provided informed consent is assessed for study eligibility.
Treatment period (Day 1 to Day 85): After screening, eligible subjects are randomly assigned to one of the following treatment arms in a 1:1:1:1:1:1:1 ratio:
10 mg compound (I) once daily
35 mg compound (I) once daily
100 mg compound (I) once daily
10 mg compound (I) twice a day
25 mg compound (I) twice a day
100 mg compound (I) twice a day
Placebo
An interim analysis is performed to assess the dose-response relationship of compound of Formula (I) after all subjects have completed their Week 4 visit (primary endpoint).
Follow-up period (Day 86 to Day 113): subjects are followed-up to assess durability of response after withdrawal of treatment and to further assess safety.

TABLE 10

| | |
|---|---|
| Prohibited medication | |
| Medication | Prohibition period |
| Biologics for treatment of CSU (including omalizumab and ligelizumab) | 4 months prior to screening until end of study |
| Routine (daily or every other day during 5 or more consecutive days) doses of systemic corticosteroids | 30 days prior to screening until end of study Note: from Day 1 (baseline) until Week 12 (end of treatment period) the use of systemic corticosteroids is not permitted at all. |
| Leukotriene antagonists (including montelukast and zafirlukast) | From screening until end of study |
| H2-antihistamines | From screening until end of study |
| First generation antihistamines | From screening until end of study |
| Second generation antihistamines other than the defined background medication and rescue medication | From screening until end of study |
| Other immunosuppressive medication with or without known effect on CSU including but not limited to hydroxychloroquine, methotrexate, cyclosporine A, cyclophosphamide, tacrolimus and mycophenolate mofetil | 30 days or 5 half-lives (whichever is longer) prior to screening until end of study |
| Intravenous (i.v.) immunoglobulins or plasmapheresis | 30 days prior to screening until end of study |
| Regular (daily or every other day) doxepin (oral) | 14 days prior to screening until end of study |
| Live attenuated vaccine | 6 weeks prior to screening until end of study |
| Any drug known to prolong QTc interval (see https://crediblemeds.org for guidance) | 5 half-lives or until pharmacodynamic effect has disappeared prior to baseline (whichever is longer) until end of study |
| Anti-platelet or anticoagulant medication (for example, warfarin, or clopidogrel or Novel Oral Anti-Coagulant-NOAC) other than acetylsalicylic acid (up to 100 mg/d) | From screening until end of study |
| Protocol summary: | |
| Purpose and rationale | The purpose of this study is to collect efficacy and safety data for compound of Formula (I) in subjects suffering from CSU inadequately controlled by H1-antihistamines |
| Secondary Objectives | To evaluate the efficacy of Compound (I) compared to placebo with respect to change from baseline UAS7 at Week 12 To evaluate the efficacy of Compound (I) compared to placebo with respect to change from baseline UAS7 over time |

TABLE 10-continued

| | Prohibited medication |
|---|---|
| Medication | Prohibition period |
| | To evaluate the efficacy of Compound (I) compared to placebo with respect to achievement of complete clinical response (UAS7 = 0) over time
To evaluate the efficacy of Compound (I) compared to placebo with respect to achievement of disease control (UAS7 ≤6) over time
To evaluate the effect of Compound (I) on angioedema (AAS7) with respect to the number of weeks with an AAS7 = 0 response from baseline through Week 12
To evaluate the effect of Compound (I) on disease-related quality of life with respect to achievement of a DLQI score of 0 or 1 at Week 4 and Week 12
To evaluate the effect of Compound (I) on CSU-related quality of life with respect to change from baseline in DLQI at Week 4 and Week 12
To evaluate the pharmacokinetics (PK) of Compound (I) resulting from oral dosing (PK sampling is performed at Week 4 and Week 12)
To evaluate safety and tolerability of Compound (I) in subjects with CSU |
| Population | The study population consist of approximately 308 female and male adult patients with at least moderately active chronic spontaneous urticaria inadequately controlled by second generation H1-antihistamines. |
| Key Inclusion criteria | Male and female adult subjects aged ≥ 18 years of age.
CSU diagnosis for ≥ 6 months prior to screening
Diagnosis of CSU inadequately controlled by second generation H1-antihistamines as defined in the following:
The presence of itch and hives for ≥ 6 consecutive weeks prior to screening in spite of use of non-sedating H1-antihistamines according to local treatment guidelines during this time period
UAS7 score (range 0-42) ≥ 16 and HSS7 score (range 0-21) ≥ 8 during 7 days prior to randomization (Day 1)
Presence of hives must have been documented within three months before randomization (either at screening and/or randomization; or documented in the subject's medical history) |
| Key Exclusion criteria | Subjects having a clearly defined predominant or sole trigger of their chronic urticaria (chronic inducible urticaria) including urticaria factitia (symptomatic dermographism), cold-, heat-, solar-, pressure-, delayed pressure-, aquagenic-, cholinergic-, or contact-urticaria
Other diseases with symptoms of urticaria or angioedema, including but not limited to urticaria vasculitis, urticaria pigmentosa, erythema multiforme, mastocytosis, hereditary urticaria, or acquired/drug-induced urticaria
Any other skin disease associated with chronic itching that might influence in the investigators opinion the study evaluations and results, eg atopic dermatitis, bullous pemphigoid, dermatitis herpetiformis, senile pruritus or psoriasis
History or current diagnosis of ECG abnormalities indicating significant risk of safety for subjects participating in the study such as:
   Concomitant clinically significant cardiac arrhythmias, eg sustained ventricular tachycardia, and clinically significant second or third degree AV block without a pacemaker
   History of familial long QT syndrome or known family history of Torsades de Pointes
   Resting heart rate (physical exam or 12 lead ECG) <60 bpm
   Resting QTcF ≥450 msec (male) or ≥460 msec (female) at pretreatment [screening]or inability to determine the QTcF interval
   Use of agents known to prolong the QT interval unless it can be permanently discontinued for the duration of study
Significant bleeding risk or coagulation disorders
Known or suspected history of an ongoing, chronic or recurrent infectious disease including but not limited to opportunistic infections (eg tuberculosis, atypical mycobacterioses, listeriosis or aspergillosis), HIV, Hepatitis B/C |
| Efficacy assessments | In this study, all efficacy measures are PROs:
Urticaria Patients Daily Diary (UPDD), including
Urticaria Activity Score (UAS)
Angioedema Activity Score (AAS)
Assessment of impact of CSU on sleep and daily activity
Dermatology Life Quality Index (DLQI) |
| Key safety assessments | Adverse event (AE) monitoring
Physical examinations
Vital signs
Monitoring of laboratory markers in blood and urine
ECG monitoring |
| Data analysis | The main purpose of this study is to characterize the dose-response relationship among Compound (I) q.d. and b.i.d doses and placebo with respect to the change from baseline in UAS7 at Week 4, and select appropriate dose(s) to use in Phase 3 studies. The consecutive steps are therefore (1) to confirm an overall dose-response signal, (2) to estimate the dose-response curve to enable selecting a dose(s) for the Phase 3 studies. The MCP-Mod (Bretz et al 2005, biometrics, 61(3):738-48, Pinheiro et al 2014; Stat Med; |

TABLE 10-continued

| Prohibited medication | |
|---|---|
| Medication | Prohibition period |
| | 33(10):1646-61, Qualification Opinion on MCP-Mod EMA 2014, FDA endorsement 2016) (methodology is used to address these goals. For secondary endpoints, summary tables are presented by treatment group and visit (as applicable) using descriptive statistics, which include absolute and relative frequencies for categorical variables and arithmetic mean, standard deviation, minimum, maximum, median and first and third quartile for continuous variables. |

Primary Endpoints

The primary variable for the study is the change from baseline in UAS7 at Week 4. The UAS7 is the sum of the average daily UAS over 7 days. Note that the weekly score is derived by using the last 7 days prior to the visit.

Secondary Endpoints

Efficacy of instant method is analyzed by treatment group and visit (as applicable) using descriptive statistics, which include absolute and relative frequencies for categorical variables and arithmetic mean, standard deviation, minimum, maximum, median and first and third quartile for continuous variables. For the secondary analysis of UAS7, complete clinical response, controlled disease and AAS7=0, pairwise comparisons of each compound (I) doses to placebo is performed.

UAS7

Summary statistics of the absolute and percent change from baseline in UAS7 is analyzed by treatment group and visit in the Treatment and Follow-up periods.

Complete Clinical Response

The complete clinical response, i.e. absence of hives and itch, is defined as subjects achieving UAS7=0.

The number of subjects with UAS7=0 by treatment group and visit in the Treatment and Follow-up periods.

Pairwise comparisons between treatment groups (individual Compound (I) arms versus placebo), Controlled Disease (UAS7≤6)

The number of subjects with UAS7≤6 by treatment group and visit in the Treatment and Follow-up periods.

Pairwise comparisons between treatment groups (individual Compound (I) arms versus placebo), Absence of Angioedema (AAS7=0)

The cumulative number of weeks with an AAS7=0 response between baseline and Week 12

It is derived based on AAS eDiary. A weekly AAS7 score is derived by adding up the daily scores of the 7 days preceding the visit, and ranges from 0 to 105. If the AAS7 assessment is missing, it is considered as a non-response for the cumulative number of weeks that subjects achieve AAS7=0 response calculation. The cumulative number of weeks achieving AAS7=0 response between baseline and Week 12 is modelled using a negative binomial regression model with log link, using treatment group, randomization strata and baseline AAS7=0 status.

DLQI

Seven scores is derived from the DLQI: the score of each of the six dimensions as well as the total score of the DLQI is calculated based on the developers' rules. For each of these seven scores the change from baseline and percentage change from baseline is also derived. Summary statistics are calculated for the absolute values as well as for the change and percentage change broken down by visit and treatment group.

number of subjects with DLQI score of 0 or 1 by treatment group and visit.

Safety Endpoints

All safety endpoints (i.e. AEs, laboratory data, vital signs, and ECG as well as potential risks defined in the safety profiling plan) are summarized by treatment for all subjects of the safety set. All data are included in the analysis regardless of rescue medication use.

The data from the clinical trial as well as preclinical evidence presented above show that Compound (I) at daily doses of 10 mg to 200 mg to be safe and pharmacological active for treatment of basophil- and mast driven-skin diseases.

What is claimed is:

1. A method of treating chronic spontaneous urticaria in a subject in need of such treatment, comprising administering to the subject a daily dose of from about 10 mg to about 100 mg of a compound of Formula (I):

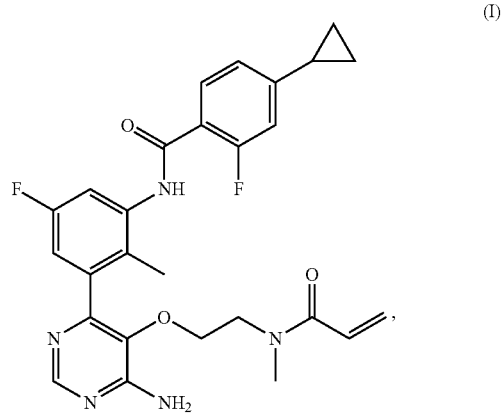 [SMILES: C=CC(=O)N(C)CCOc1c(N)ncnc1-c1cc(F)cc(NC(=O)c2ccc(C3CC3)cc2F)c1C]

or a pharmaceutically acceptable salt thereof.

2. The method of claim 1, wherein the daily dose of the compound of Formula (I) is about 100 mg.

3. The method of claim 1, wherein the daily dose of the compound of Formula (I) is about 50 mg.

4. The method of claim 3, wherein the compound of Formula (I) is administered at a dose of 25 mg twice a day to an adult.

5. The method of claim 4, wherein prior to the treatment with the compound of Formula (I), the subject has been previously treated with H1-antihistamine and remains symptomatic despite treatment with the H1-antihistamine, as defined by a presence of itch and hives for ≥6 consecutive weeks.

6. The method of claim 4, wherein prior to the treatment with the compound of Formula (I), the subject has moderate to severe chronic spontaneous urticaria as defined by a Weekly Urticaria Activity Score (UAS7) of ≥16.

7. The method of claim 4, wherein the subject achieves by week 12 of the treatment at least one of the following:
   a) a reduction of hives and itch as measured by a Urticaria Activity Score (UAS) of ≤6; or a complete absence of hives and itch as measured by a Weekly Urticaria Activity Score (UAS7) of zero;
   b) a Dermatology Life Quality Index (DLQI)=0-1; and
   c) an absence of angioedema as measured by a Weekly Angioedema Activity Score (AAS7) of zero.

8. The method of claim 3, wherein the compound of Formula (I) is administered at a dose of 50 mg once a day to an adult.

9. The method of claim 8, wherein prior to the treatment with the compound of Formula (I), the subject has been previously treated with H1-antihistamine and remains symptomatic despite treatment with the H1-antihistamine, as defined by a presence of itch and hives for ≥6 consecutive weeks.

10. The method of claim 8, wherein prior to the treatment with the compound of Formula (I), the subject has moderate to severe chronic spontaneous urticaria as defined by a Weekly Urticaria Activity Score (UAS7) score of ≥16.

11. The method of claim 8, wherein the subject achieves by week 12 of the treatment at least one of the following:
   a) a reduction of hives and itch as measured by a Urticaria Activity Score (UAS) of ≤6; or a complete absence of hives and itch as measured by a Weekly Urticaria Activity Score (UAS7) of zero;
   b) a Dermatology Life Quality Index (DLQI)=0-1; and
   c) an absence of angioedema as measured by a Weekly Angioedema Activity Score (AAS7) of zero.

12. The method of claim 1, wherein the daily dose of the compound of Formula (I) is about 35 mg.

13. The method of claim 1, wherein the daily dose of the compound of Formula (I) is about 25 mg.

14. The method of claim 1, wherein the daily dose of the compound of Formula (I) is about 20 mg.

15. The method of claim 14, wherein the compound of Formula (I) is administered at a dose of 10 mg twice a day.

16. The method of claim 15, wherein prior to the treatment with the compound of Formula (I), the subject has been previously treated with H1-antihistamine and remains symptomatic despite treatment with the H1-antihistamine, as defined by a presence of itch or hive for ≥6 consecutive weeks.

17. The method of claim 15, wherein prior to the treatment with the compound of Formula (I), the subject has moderate to severe chronic spontaneous urticaria as defined by a Weekly Urticaria Activity Score (UAS7) score of ≥16.

18. The method of claim 15, wherein the subject achieves by week 12 of the treatment at least one of the following:
   a) a reduction of hives and itch as measured by a Urticaria Activity Score (UAS) of ≤6; or a complete absence of hives and itch as measured by a Weekly Urticaria Activity Score (UAS7) of zero;
   b) a Dermatology Life Quality Index (DLQI)=0-1; and
   c) an absence of angioedema as measured by a Weekly Angioedema Activity Score (AAS7) of zero.

19. The method of claim 1, wherein the compound of Formula (I) is administered once a day at a dose of about 10 mg, about 35 mg, about 50 mg, or about 100 mg.

20. The method of claim 1, wherein the compound of Formula (I) is administered at a dose of about 10 mg, about 25 mg, or about 50 mg twice daily.

21. The method of claim 1, wherein prior to the treatment with the compound of Formula (I), or the pharmaceutically acceptable salt thereof, the subject has been previously treated with a systemic agent for chronic spontaneous urticaria.

22. The method of claim 21, wherein the systemic agent is selected from the group consisting of an H1-antihistamine, an H2-antihistamine, a leukotriene receptor antagonist, and a combination thereof.

23. The method of claim 1, wherein prior to the treatment with the compound of Formula (I), or the pharmaceutically acceptable salt thereof, the subject has not been previously treated with a systemic agent for chronic spontaneous urticaria.

24. The method of claim 1, wherein the subject has moderate to severe chronic spontaneous urticaria.

25. The method of claim 1, wherein the subject is selected according to at least one of the following criteria:
   a) prior to the treatment with the compound of Formula (I) or a pharmaceutically acceptable salt thereof, the subject has a Weekly Urticaria Activity Score (UAS7) of ≥16;
   b) prior to the treatment with the compound of Formula (I) or a pharmaceutically acceptable salt thereof, the subject has a Weekly Hives Severity Score (HSS7) ≥8.

26. The method of claim 1, wherein the subject is an adult.

27. The method of claim 1, wherein the subject achieves by week 4 or at week 12 of the treatment at least one of the following:
   a) a reduction of hives and itch as measured by a Urticaria Activity Score (UAS)≤6; or a complete absence of hives and itch as measured by a Weekly Urticaria Activity Score (UAS7) of zero;
   b) a Dermatology Life Quality Index (DLQI)=0-1; and
   c) an absence of angioedema as measured by a Weekly Angioedema Activity Score (AAS7) of zero.

28. The method of claim 1, wherein the subject achieves a sustained response as measured by at least one of the following at week 4 after completion of the treatment:
   a) a complete hives and itch response as measured by a Weekly Urticaria Activity Score (UAS7) of zero;
   b) a Dermatology Life Quality Index (DLQI)=0-1; and
   c) a continued absence of angioedema as measured by a Weekly Angioedema Activity Score (AAS7) of zero.

29. The method of claim 1, wherein the compound of Formula (I), or the pharmaceutically acceptable salt thereof, is disposed in a pharmaceutical formulation, wherein the pharmaceutical formulation further comprises a pharmaceutically acceptable carrier.

30. The method of claim 1, wherein the compound of Formula (I), or the pharmaceutically acceptable salt thereof, has a Tmax of about 0.5-3 hours.

* * * * *